United States Patent
Ding et al.

(10) Patent No.: US 7,338,957 B2
(45) Date of Patent: Mar. 4, 2008

(54) COMPOUNDS AND COMPOSITIONS AS PROTEIN KINASE INHIBITORS

(75) Inventors: Qiang Ding, San Diego, CA (US); Nathanael Schiander Gray, San Diego, CA (US); Bing Li, San Diego, CA (US); Yi Liu, San Diego, CA (US); Tetsuo Uno, San Diego, CA (US)

(73) Assignee: IRM LLC, Hamilton (BM)

( * ) Notice: Subject to any disclaimer, the term of this patent is extended or adjusted under 35 U.S.C. 154(b) by 393 days.

(21) Appl. No.: 10/927,992

(22) Filed: Aug. 26, 2004

(65) Prior Publication Data

US 2005/0159391 A1  Jul. 21, 2005

Related U.S. Application Data

(60) Provisional application No. 60/498,532, filed on Aug. 28, 2003.

(51) Int. Cl.
*C07D 487/04* (2006.01)
*A61K 31/519* (2006.01)
*A61P 35/00* (2006.01)

(52) U.S. Cl. .................. 514/265.1; 544/280

(58) Field of Classification Search ............... 544/280; 514/265.1
See application file for complete search history.

(56) References Cited

OTHER PUBLICATIONS

West, Anthony R., Solid State Chemistry and its Applications, Wiley, New York, 1988, pp. 358 & 365.*
Vippagunta et al., Advanced Drug Delivery Reviews 48: 3-26, 2001.*
Cecil Textbook of Medicine, edited by Bennet, J.C., and Plum F., 20th edition,vol. 1, 1004-1010, 1996.*
Mass, R. D., Int. J. Radiation Oncology Bio. Phys.vol. 58(3): 932-940, 2004.*
Fabbro et al. Pharmacology & therapeutics 93, 79-98, 2002.*
Vlahovic G. et al, Activation of Tyrosine Kinases in Cancer, Oncologist. 2003, vol. 8, No. 6, pp. 531-538.

* cited by examiner

*Primary Examiner*—Venkataraman Balasubram
(74) *Attorney, Agent, or Firm*—Emily Tongco Wu; Institute of the Novartis Research Foundation

(57) ABSTRACT

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the Abl, BCR-Abl, Bmx, CSK, TrkB, FGFR3, Fes, Lck, B-RAF, C-RAF, MKK6, SAPK2α and SAPK2β kinases.

8 Claims, No Drawings

COMPOUNDS AND COMPOSITIONS AS PROTEIN KINASE INHIBITORS

CROSS-REFERENCE TO RELATED APPLICATIONS

This application claims the benefit of priority under 35 U.S.C. §119(e) to U.S. Provisional Patent Application No. 60/498,532, filed Aug. 28, 2003. The disclosure of the priority application is incorporated herein by reference in its entirety and for all purposes.

BACKGROUND OF THE INVENTION

1. Field of the Invention

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the Abl, BCR-Abl, Bmx, CSK, TrkB, FGFR3, Fes, Lck, B-RAF, C-RAF, MKK6, SAPK2α and SAPK2β kinases.

2. Background

The protein kinases represent a large family of proteins, which play a central role in the regulation of a wide variety of cellular processes and maintaining control over cellular function. A partial, non-limiting, list of these kinases include: receptor tyrosine kinases such as the nerve growth factor receptor, trkB, and the fibroblast growth factor receptor, FGFR3; non-receptor tyrosine kinases such Abl and the fusion kinase BCR-Abl, Lck, Csk, Fes, Bmx and c-src; and serine/threonine kinases such as c-RAF, sgk, MAP kinases (e.g., MKK4, MKK6, etc.), SAPK2α and SAPK2β. Aberrant kinase activity has been observed in many disease states including benign and malignant proliferative disorders as well as diseases resulting from inappropriate activation of the immune and nervous systems.

The novel compounds of this invention inhibit the activity of one or more protein kinases and are, therefore, expected to be useful in the treatment of kinase-associated diseases.

SUMMARY OF THE INVENTION

In one aspect, the present invention provides compounds of Formula I:

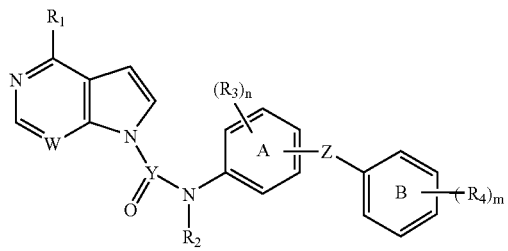

in which:
W is selected from CH and N;
Y is selected from C, S and S(O);
Z is a divalent radical selected from —Y(O)NR$_5$— and —NR$_5$Y(O)—; wherein Y is selected from C, S and S(O); and R$_5$ is selected from hydrogen and C$_{1-12}$alkyl;
R$_1$ is selected from hydrogen, halo, hydroxy C$_{1-6}$alkyl, C$_{1-6}$alkoxy and —NR$_6$R$_7$; wherein R$_6$ is selected from hydrogen and C$_{1-6}$alkyl; R$_7$ is selected from C$_{6-10}$aryl, C$_{5-10}$heteroaryl, C$_{3-12}$cycloalkyl and C$_{3-8}$heterocycloalkyl; or R$_6$ and R$_7$ together with the nitrogen to which both R$_6$ and R$_7$ are attached form C$_{3-8}$heterocycloalkyl or C$_{5-10}$heteroaryl; wherein any aryl, heteroaryl, cycloalkyl or heterocycloalkyl of R$_7$ or of the combination of R$_6$ and R$_7$ can be optionally substituted with 1 to 3 radicals selected from halo, cyano, nitro, C$_{1-6}$alkyl, C$_{2-6}$alkenyl, C$_{2-6}$alkynyl, halo-substituted-C$_{1-6}$alkyl, C$_{1-6}$alkoxy, halo-substituted-C$_{1-6}$alkoxy, —XNR$_8$R$_8$, —XC(O)NR$_8$R$_8$, —XC(O)NR$_8$XOR$_8$, —XS(O)$_{0-2}$NR$_8$R$_8$, —XS(O)$_{0-2}$R$_8$, —XNR$_8$S(O)$_{0-2}$R$_8$, —XNR$_8$C(O)R$_8$, —XNR$_8$SR$_8$, —XP(O)NR$_8$R$_8$, —XCR$^8$(OR$_8$)R$_8$, —XOC(O)R$_8$, —XOR$_8$ and —XOR$_9$; wherein X is a bond or C$_{1-12}$alkylene, R$_8$ is independently selected from hydrogen and C$_{1-6}$alkyl, R$_9$ is selected from C$_{6-10}$aryl and C$_{5-10}$heteroaryl;

R$_2$ is selected from hydrogen and C$_{1-6}$alkyl;

R$_3$ is selected from hydrogen, hydroxy, C$_{1-6}$alkyl, C$_{2-6}$alkenyl, C$_{2-6}$alkynyl, C$_{1-6}$alkoxy, mercapto, halo, nitro and cyano;

n is 0, 1 or 2;

R$_4$ is selected from hydrogen, halo, hydroxy, cyano, nitro, C$_{1-6}$alkyl, halo-substituted-C$_{1-6}$alkyl, C$_{1-12}$alkoxy, halo-substituted-C$_{1-12}$alkoxy and —XR$_{10}$; wherein X is a bond or C$_{1-6}$alkylene, R$_{10}$ is selected from C$_{6-10}$aryl, C$_{5-10}$heteroaryl, C$_{3-12}$cycloalkyl and C$_{3-8}$heterocycloalkyl; wherein any aryl, heteroaryl, cycloalkyl or heterocycloalkyl of R$_{10}$ is optionally substituted with a radical selected from halo, hydroxy, cyano, nitro, C$_{1-6}$alkyl, halo-substituted-C$_{1-6}$alkyl, C$_{1-6}$alkoxy and halo-substituted-C$_{1-6}$alkoxy;

m is 1, 2 or 3; and wherein the phenyl rings A and B can independently have up to four —C= groups replaced by —N=; and the N-oxide derivatives, prodrug derivatives, protected derivatives, individual isomers and mixture of isomers thereof, and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal, including human, in which inhibition of kinase activity, particularly the Abl, BCR-Abl, Bmx, CSK, TrkB, FGFR3, Fes, Lck, B-RAF, C-RAF, MKK6, SAPK2α and/or SAPK2β activity, can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which kinase activity, particularly the Abl, BCR-Abl, Bmx, CSK, TrkB, FGFR3, Fes, Lck, B-RAF, C-RAF, MKK6, SAPK2α and/or SAPK2β activity, contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-4}$-alkoxy includes, methoxy, ethoxy, and the like. Halo-substituted alkyl includes trifluoromethyl, pentafluoroethyl, and the like. Unless otherwise defined, "alkyl" can be optionally interrupted by —O— or optionally substituted by —OH.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group. "Heteroaryl" is as defined for aryl where one or more of the ring members are a heteroatom. For example heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc. "Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, piperazinyl, piperidinyl, piperidinylone, 1,4-dioxa-8-aza-spiro[4.5]dec-8-yl, etc.

"Halogen" (or halo) preferably represents chloro or fluoro, but may also be bromo or iodo.

"Treat", "treating" and "treatment" refer to a method of alleviating or abating a disease and/or its attendant symptoms.

DESCRIPTION OF THE PREFERRED EMBODIMENTS

The fusion protein BCR-Abl is a result of a reciprocal translocation that fuses the Abl proto-oncogene with the Bcr gene. BCR-Abl is then capable of transforming B-cells through the increase of mitogenic activity. This increase results in a reduction of sensitivity to apoptosis, as well as altering the adhesion and homing of CML progenitor cells. The present invention provides compounds, compositions and methods for the treatment of kinase related disease, particularly the Abl, BCR-Abl, Bmx, CSK, TrkB, FGFR3, Fes, Lck, B-RAF, C-RAF, MKK6, SAPK2α and/or SAPK2β kinase related diseases. For example, leukemia and other proliferation disorders related to BCR-Abl can be treated through the inhibition of wild type and mutant forms of BCR-Abl.

In one embodiment, with reference to compounds of Formula I, W is N; Y is C; Z is a divalent radical selected from —C(O)NR$_5$— and —NR$_5$C(O)—; wherein R$_5$ is selected from hydrogen and $C_{1-6}$alkyl;

In another embodiment, is selected from hydrogen, halo, hydroxy and —NR$_6$R$_7$; wherein R$_6$ is selected from hydrogen and $C_{1-6}$alkyl; R$_7$ is selected from $C_{6-10}$aryl and $C_{5-10}$heteroaryl; or R$_6$ and R$_7$ together with the nitrogen to which both R$_6$ and R$_7$ are attached form $C_{3-8}$heterocycloalkyl; wherein any aryl, heteroaryl or heterocycloalkyl of R$_7$ or of the combination of R$_6$ and R$_7$ can be optionally substituted with 1 to 3 radicals selected from halo, cyano, $C_{1-6}$alkyl, $C_{2-6}$alkenyl, halo-substituted-$C_{1-6}$alkyl, halo-substituted-$C_{1-6}$alkoxy, —XNR$_8$R$_8$, —XC(O)NR$_8$R$_8$, —XC(O)NR$_8$XOR$_8$, —XS(O)$_2$NR$_8$R$_8$, —XSR$_8$, —XNR$_8$S(O)$_2$R$_8$, —XNR$_8$C(O)R$_8$, —XOC(O)R$_8$, —XOR$_8$ and —XOR$_9$; wherein X is a bond or $C_{1-6}$alkylene, R$_8$ is hydrogen or $C_{1-6}$alkyl, R$_9$ is $C_{6-10}$aryl;

In a further embodiment, R$_2$ is selected from hydrogen and $C_{1-6}$alkyl; R$_3$ is $C_{1-6}$alkyl; n is 1; and R$_4$ is selected from halo, halo-substituted-$C_{1-6}$alkyl and —XR$_{10}$; wherein X is a bond or $C_{1-6}$alkylene, R$_{10}$ is selected from $C_{5-10}$heteroaryl and $C_{3-8}$heterocycloalkyl; wherein any heteroaryl or heterocycloalkyl of R$_{10}$ is optionally substituted with $C_{1-6}$alkyl; and m is 1, 2 or 3.

In another embodiment, Z is a divalent radical selected from —C(O)NH— and —NHC(O)—.

In another embodiment, R$_1$ is selected from hydrogen, halo, hydroxy and —NHR$_7$; wherein R$_7$ is selected from phenyl and pyridinyl; or R$_6$ and R$_7$ together with the nitrogen to which both R$_6$ and R$_7$ are attached form morpholino; wherein any aryl, heteroaryl or heterocycloalkyl of R$_7$ or of the combination of R$_6$ and R$_7$ can be optionally substituted with 1 to 3 radicals selected from halo, cyano, trifluoromethyl, trifluoromethoxy, dimethylamino, amino, aminocarbonyl, methyl-aminocarbonyl, aminosulfonyl, 1-hydroxyethyl, hydroxymethyl, acetoxy-methyl, methyl-sulfanyl, phenoxy, methyl-carboxy-methyl, butyl-amino-sulfonyl, methyl, isopropenyl, methoxy-ethyl-amino-carbonyl, 1-hydroxy-1-methyl-ethyl, methyl-sulfonyl-amino and methyl-carbonyl-amino; and R$_3$ is hydrogen or methyl.

In a further embodiment, R$_4$ is selected from halo, trifluoromethyl and —XR$_{10}$; wherein X is a bond or methylene; R$_{10}$ is selected from imidazolyl, piperazinyl and morpholino; wherein any heteroaryl or heterocycloalkyl is optionally substituted with methyl.

Preferred compounds of the invention are selected from: 4-(3-Trifluoromethyl-phenylamino)-pyrrolo[2,3-d]pyrimidine-7-carboxylic acid [3-(4-morpholin-4-yl-phenylcarbamoyl)-phenyl]-amide; 4-(4-Trifluoromethyl-1-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(3-Dimethylamino-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-(3-Carbamoyl-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(3-Sulfamoyl-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-[3-(1-Hydroxy-ethyl)-phenylamino]-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-(3-Carbamoyl-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-(3-Sulfamoyl-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-[3-(1-Hydroxy-ethyl)-phenylamino]-pyrrolo[2,3-d]pyrimidine-7-carboxylic acid [5-(3-fluoro-5-trifluoromethyl-benzoylamino)-2-methyl-phenyl]-amide; 4-Hydroxy-pyrrolo[2,3-d]pyrimidine-7-carboxylic acid {2-methyl-5-[3-

(4-methyl-imidazol-1-yl)-5-trifluoromethyl-benzoylamino]-phenyl}-amide; 4-(4-Carbamoyl-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-(3-Hydroxymethyl-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; Acetic acid 3-(7-{2-methyl-5-[3-(4-methyl-imidazol-1-yl)-5-trifluoromethyl-benzoylamino]-phenylcarbamoyl}-7H-pyrrolo[2,3-d]pyrimidin-4-ylamino)-benzyl ester; Pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-(4-Trifluoromethyl-phenylamino)-pyrrolo[2,3-d]pyrimidine-7-carboxylic acid [3-(4-morpholin-4-yl-phenylcarbamoyl)-phenyl]-amide; 4-(4-Trifluoromethyl-phenylamino)-pyrrolo[2,3-d]pyrimidine-7-carboxylic acid [4-(4-morpholin-4-yl-phenylcarbamoyl)-phenyl]-amide; 4-(4-Trifluoromethoxy-phenylamino)-pyrrolo[2,3-d]pyrimidine-7-carboxylic acid [3-(4-morpholin-4-yl-phenylcarbamoyl)-phenyl]-amide; 4-(3-Bromo-phenylamino)-pyrrolo[2,3-d]pyrimidine-7-carboxylic acid [3-(4-morpholin-4-yl-phenylcarbamoyl)-phenyl]-amide; 4-(3-Dimethylamino-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(3-Bromo-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(3-Methylsulfanyl-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(Pyridin-3-ylamino)-pyrrolo[2,3-d]pyrimidine-7-carboxylic acid {2-methyl-5-[4-(4-methyl-piperazin-1-ylmethyl)-benzoylamino]-phenyl}-amide; 4-(3-Phenoxy-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(3-Hydroxymethyl-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(3-Butylsulfamoyl-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(4-Fluoro-2-methyl-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(3-Chloro-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(3-Fluoro-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-m-Tolylamino-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-(3-Cyano-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-Chloro-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-Chloro-pyrrolo[2,3-d]pyrimidine-7-carboxylic acid {2-methyl-5-[4-(4-methyl-piperazin-1-ylmethyl)-benzoylamino]-phenyl}-amide; Acetic acid 3-(7-{2-methyl-5-[4-(4-methyl-piperazin-1-ylmethyl)-benzoylamino]-phenylcarbamoyl}-7H-cyclopentapyrimidin-4-ylamino)-benzyl ester; 4-(3-Isopropenyl-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-[3-(2-Methoxy-ethylcarbamoyl)-phenylamino]-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-[3-(1-Hydroxy-1-methyl-ethyl)-phenylamino]-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-[3-(1-Hydroxy-ethyl)-phenylamino]-pyrrolo[2,3-d]pyrimidine-7-carboxylic acid [5-(3-fluoro-5-trifluoromethyl-benzoylamino)-2-methyl-phenyl]-amide; 4-Chloro-pyrrolo[2,3-d]pyrimidine-7-carboxylic acid [2-methyl-5-(3-trifluoromethyl-benzoylamino)-phenyl]-amide; 4-Hydroxy-pyrrolo[2,3-d]pyrimidine-7-carboxylic acid [2-methyl-5-(3-trifluoromethyl-benzoylamino)-phenyl]-amide; 4-(3-Dimethylamino-phenylamino)-pyrrolo[2,3-d]pyrimidine-7-carboxylic acid [2-methyl-5-(3-trifluoromethyl-benzoylamino)-phenyl]-amide; 4-[3-(1-Hydroxy-ethyl)-phenylamino]-pyrrolo[2,3-d]pyrimidine-7-carboxylic acid [2-methyl-5-(3-trifluoromethyl-benzoylamino)-phenyl]-amide; 4-(3-Hydroxymethyl-phenylamino)-pyrrolo[2,3-d]pyrimidine-7-carboxylic acid [2-methyl-5-(3-trifluoromethyl-benzoylamino)-phenyl]-amide; 4-(3-Carbamoyl-phenylamino)-pyrrolo[2,3-d]pyrimidine-7-carboxylic acid [2-methyl-5-(3-trifluoromethyl-benzoylamino)-phenyl]-amide; 4-(3-Methanesulfonylamino-phenylamino)-pyrrolo[2,3-d]pyrimidine-7-carboxylic acid [2-methyl-5-(3-trifluoromethyl-benzoylamino)-phenyl]-amide; 4-(3-Acetylamino-phenylamino)-pyrrolo[2,3-d]pyrimidine-7-carboxylic acid [2-methyl-5-(3-trifluoromethyl-benzoylamino)-phenyl]-amide; 4-(3-Sulfamoyl-phenylamino)-pyrrolo[2,3-d]pyrimidine-7-carboxylic acid [2-methyl-5-(3-trifluoromethyl-benzoylamino)-phenyl]-amide; 4-(4-Carbamoyl-phenylamino)-pyrrolo[2,3-d]pyrimidine-7-carboxylic acid [2-methyl-5-(3-trifluoromethyl-benzoylamino)-phenyl]-amide; 4-(3-Methylcarbamoyl-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-(3-Acetylamino-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-(3-Methanesulfonylamino-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-Morpholin-4-yl-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-Morpholin-4-yl-pyrrolo[2,3-d]pyrimidine-7-carboxylic acid [5-(3-fluoro-5-trifluoromethyl-benzoylamino)-2-methyl-phenyl]-amide; 4-(3-Dimethylamino-phenylamino)-pyrrolo[2,3-d]pyrimidine-7-carboxylic acid (3-{[3-(4-methyl-imidazol-1-yl)-5-trifluoromethyl-benzoylamino]-methyl}-phenyl)-amide; and 4-(3-Dimethylamino-phenylamino)-pyrrolo[2,3-d]pyrimidine-7-carboxylic acid {2-methyl-3-[3-(4-methyl-imidazol-1-yl)-5-trifluoromethyl-benzoylamino]-phenyl}-amide.

Further preferred compounds of Formula I are detailed in the Examples and Table 1, infra.

PHARMACOLOGY AND UTILITY

Compounds of the invention modulate the activity of protein tyrosine kinases and, as such, are useful for treating diseases or disorders in which protein tyrosine kinases, particularly the Abl, BCR-Abl, Bmx, CSK, TrkB, FGFR3, Fes, Lck, B-RAF, C-RAF, MKK6, SAPK2α and SAPK2β kinases, contribute to the pathology and/or symptomology of the disease.

Abelson tyrosine kinase (i.e. Abl, c-Abl) is involved in the regulation of the cell cycle, in the cellular response to genotoxic stress, and in the transmission of information about the cellular environment through integrin signaling. Overall, it appears that the Abl protein serves a complex role as a cellular module that integrates signals from various extracellular and intracellular sources and that influences decisions in regard to cell cycle and apoptosis. Abelson tyrosine kinase includes sub-types derivatives such as the chimeric fusion (oncoprotein) BCR-Abl with deregulated tyrosine kinase activity or the v-Abl. BCR-Abl is critical in the pathogenesis of 95% of chronic myelogenous leukemia (CML) and 10% of acute lymphocytic leukemia. STI-571 (Gleevec) is an inhibitor of the oncogenic BCR-Abl tyrosine kinase and is used for the treatment of chronic myeloid leukemia (CML). However, some patients in the blast crisis stage of CML are resistant to STI-571 due to mutations in the BCR-Abl kinase. Over 22 mutations have been reported to date with the most common being G250E, E255V, T315I, F317L and M351T.

Compounds of the present invention inhibit abl kinase, especially v-abl kinase. The compounds of the present invention also inhibit wild-type BCR-Abl kinase and mutations of BCR-Abl kinase and are thus suitable for the treatment of Bcr-abl-positive cancer and tumor diseases, such as leukemias (especially chronic myeloid leukemia and acute lymphoblastic leukemia, where especially apoptotic mechanisms of action are found), and also shows effects on the subgroup of leukemic stem cells as well as potential for the purification of these cells in vitro after removal of said cells (for example, bone marrow removal) and reimplantation of the cells once they have been cleared of cancer cells (for example, reimplantation of purified bone marrow cells).

The trk family of neurotrophin receptors (trkA, trkB, trkC) promotes the survival, growth and differentiation of the neuronal and non-neuronal tissues. The TrkB protein is expressed in neuroendocrine-type cells in the small intestine and colon, in the alpha cells of the pancreas, in the monocytes and macrophages of the lymph nodes and of the spleen, and in the granular layers of the epidermis (Shibayama and Koizumi, 1996). Expression of the TrkB protein has been associated with an unfavorable progression of Wilms tumors and of neuroblastomas. TkrB is, moreover, expressed in cancerous prostate cells but not in normal cells. The signaling pathway downstream of the trk receptors involves the cascade of MAPK activation through the Shc, activated Ras, ERK-1 and ERK-2 genes, and the PLC-gammal transduction pathway (Sugimoto et al., 2001).

The Tec family kinase, Bmx, a non-receptor protein-tyrosine kinase, controls the proliferation of mammary epithelial cancer cells.

Fibroblast growth factor receptor 3 (FGFR3) was shown to exert a negative regulatory effect on bone growth and an inhibition of chondrocyte proliferation. Thanatophoric dysplasia is caused by different mutations in fibroblast growth factor receptor 3, and one mutation, TDII FGFR3, has a constitutive tyrosine kinase activity which activates the transcription factor Stat1, leading to expression of a cell-cycle inhibitor, growth arrest and abnormal bone development (Su et al., Nature, 1997, 386, 288-292). FGFR3 is also often expressed in multiple myeloma-type cancers.

Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis.

JNKs, along with other MAPKs, have been implicated in having a role in mediating cellular response to cancer, thrombin-induced platelet aggregation, immunodeficiency disorders, autoimmune diseases, cell death, allergies, osteoporosis and heart disease. The therapeutic targets related to activation of the JNK pathway include chronic myelogenous leukemia (CML), rheumatoid arthritis, asthma, osteoarthritis, ischemia, cancer and neurodegenerative diseases. As a result of the importance of JNK activation associated with liver disease or episodes of hepatic ischemia, compounds of the invention may also be useful to treat various hepatic disorders. A role for JNK in cardiovascular disease such as myocardial infarction or congestive heart failure has also been reported as it has been shown JNK mediates hypertrophic responses to various forms of cardiac stress. It has been demonstrated that the JNK cascade also plays a role in T-cell activation, including activation of the IL-2 promoter. Thus, inhibitors of JNK may have therapeutic value in altering pathologic immune responses. A role for JNK activation in various cancers has also been established, suggesting the potential use of JNK inhibitors in cancer. For example, constitutively activated JNK is associated with HTLV-1 mediated tumorigenesis [Oncogene 13:135-42 (1996)]. JNK may play a role in Kaposi's sarcoma (KS). Other proliferative effects of other cytokines implicated in KS proliferation, such as vascular endothelial growth factor (VEGF), IL-6 and TNFα, may also be mediated by JNK. In addition, regulation of the c-jun gene in p210 BCR-ABL transformed cells corresponds with activity of JNK, suggesting a role for JNK inhibitors in the treatment for chronic myelogenous leukemia (CML) [Blood 92:2450-60 (1998)].

Certain abnormal proliferative conditions are believed to be associated with raf expression and are, therefore, believed to be responsive to inhibition of raf expression. Abnormally high levels of expression of the raf protein are also implicated in transformation and abnormal cell proliferation. These abnormal proliferative conditions are also believed to be responsive to inhibition of raf expression. For example, expression of the c-raf protein is believed to play a role in abnormal cell proliferation since it has been reported that 60% of all lung carcinoma cell lines express unusually high levels of c-raf mRNA and protein. Further examples of abnormal proliferative conditions are hyper-proliferative disorders such as cancers, tumors, hyperplasia, pulmonary fibrosis, angiogenesis, psoriasis, atherosclerosis and smooth muscle cell proliferation in the blood vessels, such as stenosis or restenosis following angioplasty. The cellular signaling pathway of which raf is a part has also been implicated in inflammatory disorders characterized by T-cell proliferation (T-cell activation and growth), such as tissue graft rejection, endotoxin shock, and glomerular nephritis, for example.

The stress activated protein kinases (SAPKs) are a family of protein kinases that represent the penultimate step in signal transduction pathways that result in activation of the c-jun transcription factor and expression of genes regulated by c-jun. In particular, c-jun is involved in the transcription of genes that encode proteins involved in the repair of DNA that is damaged due to genotoxic insults. Therefore, agents that inhibit SAPK activity in a cell prevent DNA repair and sensitize the cell to agents that induce DNA damage or inhibit DNA synthesis and induce apoptosis of a cell or that inhibit cell proliferation.

Mitogen-activated protein kinases (MAPKs) are members of conserved signal transduction pathways that activate transcription factors, translation factors and other target molecules in response to a variety of extracellular signals. MAPKs are activated by phosphorylation at a dual phosphorylation motif having the sequence Thr-X-Tyr by mitogen-activated protein kinase kinases (MKKs). In higher eukaryotes, the physiological role of MAPK signaling has been correlated with cellular events such as proliferation, oncogenesis, development and differentiation. Accordingly, the ability to regulate signal transduction via these pathways (particularly via MKK4 and MKK6) could lead to the development of treatments and preventive therapies for human diseases associated with MAPK signaling, such as inflammatory diseases, autoimmune diseases and cancer.

Csk down-regulates kinase activity by phosphorylating a single tyrosine residue in the C-terminus of the Src enzymes (Okada et al., J. Biol. Chem. 266:24249-24252, 1991; and Bergman et al., EMBO J. 11:2919-2924, 1992). Owing to this premier regulatory function, Csk has direct effects on many biological functions including T cell activation, neuronal development, cytoskeletal organization, and cell cycle control.

Examples of the diseases associated with activity of the non-receptor tyrosine kinase from the Fes family include, but are not limited to, tumors of mesenchymal origin and tumors of hematopoietic origin.

In accordance with the foregoing, the present invention further provides a method for preventing or treating any of the diseases or disorders described above in a subject in need of such treatment, which method comprises administering to said subject a therapeutically effective amount (See, "Administration and Pharmaceutical Compositions", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other immunomodulatory or anti-inflammatory substances, for example when used in combination with cyclosporin, rapamycin, or ascomycin, or immunosuppressant analogues thereof, for example cyclosporin A (CsA), cyclosporin G, FK-506, rapamycin, or comparable compounds, corticosteroids, cyclophosphamide, azathioprine, methotrexate, brequinar, leflunomide, mizoribine, mycophenolic acid, mycophenolate mofetil, 15-deoxyspergualin, immunosuppressant antibodies, especially monoclonal antibodies for leukocyte receptors, for example MHC, CD2, CD3, CD4, CD7, CD25, CD28, B7, CD45, CD58 or their ligands, or other immunomodulatory compounds, such as CTLA4Ig. Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

PROCESSES FOR MAKING COMPOUNDS OF THE INVENTION

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999, $3^{rd}$ Edition.

Compounds of Formula I, in which $R_1$ is —$NR_6R_7$, can be prepared by proceeding as in the following Reaction Scheme I:

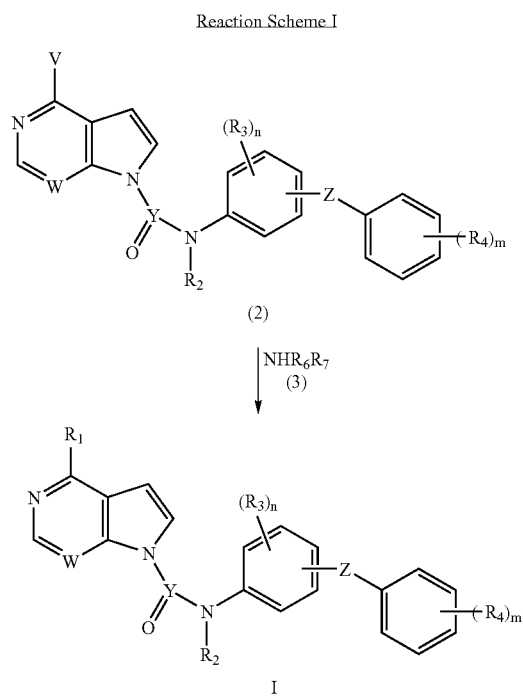

in which $R_1$, $R_2$, $R_3$, $R_4$, W, Y, Z, m and n are as defined for Formula I in the Summary of the Invention and V represents a methylsulfonyl group, or a halo group, for example iodo or chloro, preferably chloro.

A compound of Formula I can be prepared by reacting a compound of formula 2 with a compound of formula 3 in the presence of a suitable solvent (e.g., n-butanol, acetic acid, or the like), at a temperature range of 60 to 80° C. and can take up to 36 hours to complete.

Compounds of Formula I, in which Y is carbon, can be prepared by proceeding as in the following Reaction Scheme II:

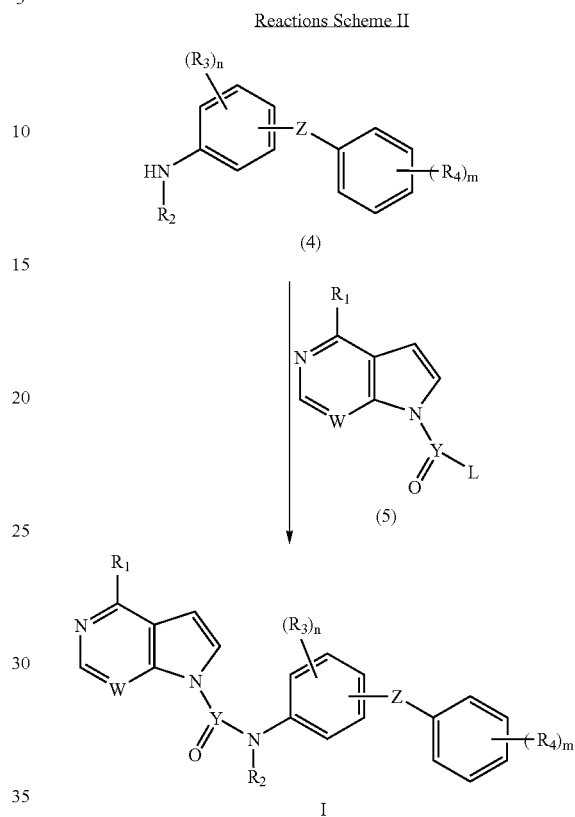

in which $R_1$, $R_2$, $R_3$, $R_4$, W, Z, m and n are as defined for Formula I in the Summary of the Invention and L is a leaving group.

A compound of formula I can be prepared by reacting a compound of formula 4 with a compound of formula 5 in the presence of an appropriate solvent (e.g., THF, and the like), using triphosgene or phosgene and an appropriate base (e.g., DIEA, and the like), at a temperature range of 0° C. to about 90° C. and can take up to 24 hours to complete.

Reactions Schemes I and II are exemplified in the references and examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.)

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. Additionally enantiomers can be separated by a chiral preparative HPLC or using enantiomerically pure reagents. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) those of reaction schemes I and II; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;
(f) optionally resolving an individual isomer of a compound of the invention from a mixture of isomers;
(g) optionally converting a non-derivatized compound of the invention into a pharmaceutically acceptable prodrug derivative; and
(h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The following examples provide detailed descriptions of the preparation of intermediates (References) and representative compounds of the invention (Examples) and are offered to illustrate, but not to limit the present invention.

Reference 1

4-Chloro-pyrrolo[2,3-d]pyrimidine-7-carboxylic acid [4-(4-morpholin-4-yl-phenylcarbamoyl)-phenyl]-amide resin

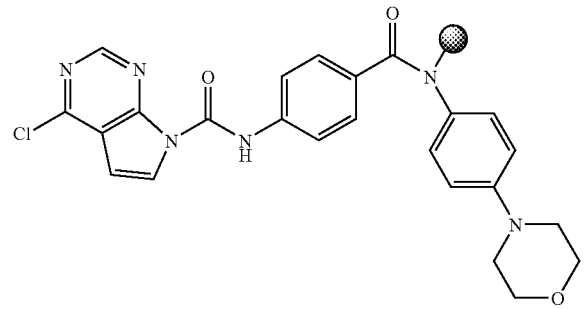

PAL-resin (Midwest Bio-Tech) bearing 4-morpholino aniline (1 g, 1 mmol), DIEA (1.04 mL, 6 mmol), and nitrobenzoyl chloride (3 mmol) are mixed in CH$_2$Cl$_2$ (10 mL) and the solution is shaken at room temperature for 16 hours. The resultant mixture is filtered and the resin is washed with DMF (3×10 mL), CH$_2$Cl$_2$ (3×10 mL), MeOH (3×10 mL) and dried under vacuum. The resin (10 mgs) is treated with TFA/CH$_2$Cl$_2$/H$_2$O (45/50/5) (200 µL) for 30 minutes. LC-MS revealed only one peak: observed MS (M+H$^+$) is 328.1; calculated MS (M+H$^+$) is 328.12.

The resulting resin is mixed with SnCl$_2$.2H$_2$O (2.26 g, 10 mmol) in NMP (10 mL), and is shaken for 48 hours. The solution is filtered and the resin is washed with NMP (3×10 mL), CH$_2$Cl$_2$ (3×10 mL), MeOH (3×10 mL), and dried under vacuum to give solid-supported 4-amino-N-(4-morpholin-4-yl-phenyl)-benzamide. This resin (10 mgs) is treated with TFA/CH$_2$Cl$_2$/H$_2$O (45/50/5) (200 µL) for 30 minutes. LC-MS revealed only one peak: observed MS (M+H$^+$) is 298.1; calculated MS (M+H$^+$) is 298.15.

6-Chloro-7-deazapurine (300 mg, 2 mmol), triphosgene (290 mg, 1 mmol), and DIEA (680 µL, 3.9 mmol) are stirred in THF (10 mL) at 0° C. for 2 hours. THF is removed by evaporation and the residue is dissolved in THF (10 mL). The solution is mixed with 4-amino-N-(4-morpholin-4-yl-phenyl)-benzamide resin and shaken for 18 hours. The solution is filtered and the resin is washed with DMF (3×10 mL), CH$_2$Cl$_2$ (3×10 mL), MeOH (3×10 mL), and dried under vacuum to give 4-chloro-pyrrolo[2,3-d]pyrimidine-7-carboxylic acid-[4-(4-morpholin-4-yl-phenylcarbamoyl)-phenyl]-amide resin. 10 mgs of the resin is further treated with TFA/CH$_2$Cl$_2$/H$_2$O (45/50/5) (200 μL) for 30 minutes. LC-MS showed only one peak: observed MS (M+H$^+$) is 477.10; calculated MS (M+H$^+$) is 477.14. 4-Chloro-pyrrolo[2,3-d]pyrimidine-7-carboxylic acid methyl-[4-(3-morpholin-4-yl-phenylcarbamoyl)-phenyl]-amide resin and 4-chloro-pyrrolo[2,3-d]pyrimidine-7-carboxylic acid [3-(4-morpholin-4-yl-phenylcarbamoyl)-phenyl]-amide are prepared in a similar manner using appropriate starting materials.

Reference 2

4-Chloro-pyrrolo[2,3-d]pyrimidine-7-carboxylic acid {2-methyl-5-[4-(4-methyl-piperazin-1-ylmethyl)-benzoylamino]-phenyl}-amide resin

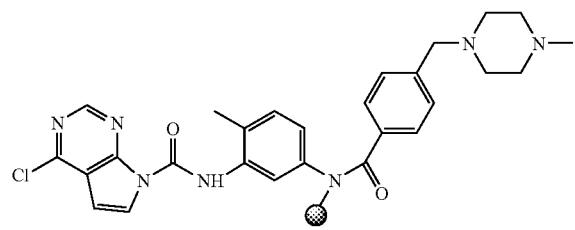

4-Methyl-3-nitro-analine PAL-resin (5 g, 5 mmol), DIEA (5.34 mL, 20 mmol), and 4-(chloromethyl)-benzoyl chloride (1.89 g, 10 mmol) are mixed in CH$_2$Cl$_2$ (50 mL) and shaken at room temperature for 18 hours. The solution is filtered and the resin is washed with DMF (3×50 mL), CH$_2$Cl$_2$ (3×50 mL), MeOH (3×50 mL) before drying under vacuum. This resin (10 mgs) is treated with TFA/CH$_2$Cl$_2$/H$_2$O (45/50/5) (200 μL) for 30 minutes. LC-MS shows one major peak: observed MS (M+H$^+$) is 305.0; calculated MS (M+H$^+$) is 304.06.

The resin is mixed with 1-methylpiperazine (5.56 mL, 49.2 mmol) in DMSO (50 mL) and shaken overnight before filtering, washing with DMF (3×50 mL), CH$_2$Cl$_2$ (3×50 mL), MeOH (3×50 mL) and drying under vacuum. This resin (10 mgs) is treated with TFA/CH$_2$Cl$_2$/H$_2$O (45/50/5) (200 μL) for 30 minutes. LC-MS shows only one peak: observed MS (M+H$^+$) is 369.2; calculated MS (M+H$^+$) is 369.18.

The resulting resin is mixed with SnCl$_2$.2H$_2$O (11.3 g, 50 mmol) in NMP (50 mL), and is shaken for 48 hours. The solution is filtered and the resin is washed with NMP (3×50 mL), CH$_2$Cl$_2$ (3×50 mL), MeOH (3×50 mL), and dried under vacuum to give solid-supported N-(3-amino-4-methyl-phenyl)-N-methyl-4-(4-methyl-piperazin-1-ylmethyl)-benzamide. This resin (10 mgs) is treated with TFA/CH$_2$Cl$_2$/H$_2$O (45/50/5) (200 μL) for 30 minutes. LC-MS shows only one peak: observed MS (M+H$^+$) is 339.2; calculated MS (M+H$^+$) is 339.21.

6-Chloro-7-deazapurine (1.50 g, 10 mmol), triphosgene (1.45 g, 5 mmol), and DIEA (3.4 mL, 19.5 mmol) are stirred in THF (50 mL) at 0° C. for 3 hours. After removing THF by evaporation, the residue is dissolved in THF (50 mL) and the solution is mixed with N-(3-amino-4-methyl-phenyl)-N-methyl-4-(4-methyl-piperazin-1-ylmethyl)-benzamide resin and shaken for 18 hours. The solution is filtered and the resin is washed with DMF (3×50 mL), CH$_2$Cl$_2$ (3×50 mL), MeOH (3×50 mL), and dried under vacuum to give 4-chloro-pyrrolo[2,3-d]pyrimidine-7-carboxylic acid {2-methyl-5-[4-(4-methyl-piperazin-1-ylmethyl)-benzoylamino]-phenyl}-amide resin. This resin (10 mgs) is treated with TFA/CH$_2$Cl$_2$/H$_2$O (45/50/5) (200 μL) for 30 minutes. LC-MS: observed MS (M+H$^+$) is 518.20; calculated MS (M+H$^+$) is 518.2.

Reference 3

4-Chloro-pyrrolo[2,3-d]pyrimidine-7-carboxylic acid {2-methyl-5-[3-(4-methyl-imidazol-1-yl)-5-trifluoromethyl-benzoylamino]-phenyl}-amide resin

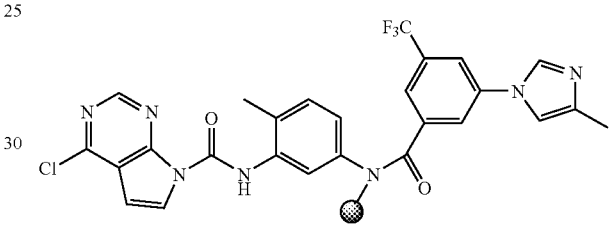

PAL-resin 4-methyl-3-nitro-aniline (5 g, 5 mmol), bis(2-oxo-3-oxazolidinyl)phosphinic chloride (5.09 g, 20 mmol), DIEA (3.5 mL, 20 mmol), and 3-(4-methyl-imidazol-1-yl)-5-trifluoromethyl-benzoic acid (2.71 g, 10.0 mmol) are mixed in DMF (50 mL) with shaking at room temperature for 18 hours. The resultant mixture is filtered and the resin is washed with DMF (3×50 mL), CH$_2$Cl$_2$ (3×50 mL), MeOH (3×50 mL), and dried under vacuum. 10 mgs of this resin is treated with TFA/CH$_2$Cl$_2$/H$_2$O (45/50/5) (200 μL) for 30 minutes. LC-MS shows only one peak: observed MS (M+H$^+$) is 405.1; calculated MS (M+H$^+$) is 405.11.

The resulting resin is mixed with SnCl$_2$.2H$_2$O (11.3 g, 50 mmol) in NMP (50 mL), and shaken at room temperature for 48 hours. The solution is filtered and the resin is washed with NMP (3×50 ml), CH$_2$Cl$_2$ (3×50 ml), MeOH (3×50 mL), and dried under vacuum to give N-(3-Amino-4-methyl-phenyl)-3-(4-methyl-imidazol-1-yl)-5-trifluoromethyl-benzamide resin. This resin (10 mgs) is treated with TFA/CH$_2$Cl$_2$/H$_2$O (45/50/5) (200 μL) for 30 minutes. LC-MS shows only one peak: observed MS (M+H$^+$) is 375.1; calculated MS (M+H$^+$) is 375.14.

6-Chloro-7-deazapurine (1.50 g, 10.0 mmol), triphosgene (1.45 g, 5.00 mmol), and DIEA (3.4 mL, 20 mmol) are stirred in THF (50 mL) at 0° C. for 3 hours. The THF is removed by evaporation, the residue is dissolved in THF (50 mL) and the solution is mixed with Pal N-(3-amino-4-methyl-phenyl)-3-(4-methyl-imidazol-1-yl)-5-trifluoromethyl-benzamide resin (5 g, 5 mmol) with shaking at room temperature for 18 hours. The solution is filtered and the resin is washed with DMF (3×50 ml), CH$_2$Cl$_2$ (3×50 ml), MeOH (3×50 mL) and dried under vacuum to give 4-Chloro-pyrrolo[2,3-d]pyrimidine-7-carboxylic acid {2-methyl-5-[3-(4-methyl-imidazol-1-yl)-5-trifluoromethyl-benzoylamino]-phenyl}-amide resin. This resin (10 mgs) is treated with TFA/CH$_2$Cl$_2$/H$_2$O (45/50/5) (200 μL) for 30 minutes. LC-MS shows only one peak: observed MS (M+H$^+$) is 554.1; calculates MS (M+H$^+$) is 554.12.

Reference 4

A solution phase synthesis of Reference 3 is achieved by mixing 3-nitro-4-methylaniline (3.00 g, 11.1 mmol), O-(7-azabenzotriazol-1-yl)-N,N,N',N'-tetramethyluronium hexafluorophosphate (5.49 g, 14.4 mmol), DIEA (5.00 mL, 28.8 mmol), and 3-(4-methyl-imidazol-1-yl)-5-trifluoro-methyl-benzoic acid (2.02 g, 13.3 mmol) in DMF (15 mL) with stirring at room temperature for 12 hours. Water (150 mL) is added into the solution and the light yellow precipitate is filtered, washed with water and dried under vacuum to give 4.3 g of product (yield 97%). LC-MS showed only one peak: observed MS (M+H$^+$) is 405.1; calculated MS (M+H$^+$) is 405.11.

The light yellow solid is stirred with 10-wt % Pd/C (600 mg) in MeOH (50 mL) under H$_2$. After 24 hours, the suspended solution is filtered and the Pd/C is washed with MeOH (3×50 mL). The combined MeOH solution is concentrated and dried under vacuum to give N-(3-amino-4-methyl-phenyl)-3-(4-methyl-imidazol-1-yl)-5-trifluoromethyl-benzamide (3.5 g yield 84%). LC-MS shows one peak: observed MS (M+H$^+$) is 375.1; calculated MS (M+H$^+$) is 375.14.

6-Chloro-7-deazapurine (3.9 g, 25.5 mmol), triphosgene (3.80 g, 12.8 mmol), and DIEA (8.9 mL, 51 mmol) are stirred in THF (100 mL) at 0° C. for 3 hours. The THF is removed by evaporation and the residue is dissolved in THF (100 mL). The solution is mixed with N-(3-amino-4-methyl-phenyl)-3-(4-methyl-imidazol-1-yl)-5-trifluoromethyl-benzamide (3.5 g, 9.3 mmol) and shaken at room temperature for 18 hours. The solvent is evaporated and the residue is purified by silica gel column chromatography (2% MeOH in CH$_2$Cl$_2$) to obtain 4-chloro-pyrrolo[2,3-d]pyrimidine-7-carboxylic acid {2-methyl-5-[3-(4-methyl-imidazol-1-yl)-5-trifluoromethyl-benzoylamino]-phenyl}-amide (3.4 g, yield 65%). $^1$H NMR (400 MHz, DMSO-d$_6$) δ 11.07 (s, 1H), 10.71 (s, 1H), 9.62 (s, 1H), 8.99 (s, 1H), 8.62 (s, 1H), 8.55 (s, 1H), 8.46 (d, J=4.0 Hz, 1H), 8.24 (d, J=4.0 Hz, 1H), 8.18 (s, 1H), 7.62 (d, J=8.0 Hz, 1H), 7.35 (d, J=8.0 Hz, 1H), 6.96 (d, J=4.0 Hz, 1H), 2.47 (s, 3H), 2.37 (s, 3H); ESIMS m/z 554.1 (M$^+$+1).

Example 1

4-(3-Trifluoromethyl-phenylamino)-pyrrolo[2,3-d]pyrimidine-7-carboxylic acid [3-(4-morpholin-4-yl-phenylcarbamoyl)-phenyl]-amide

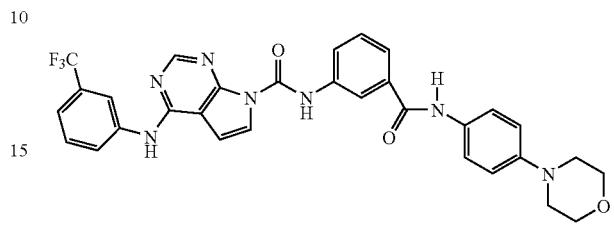

4-Chloro-pyrrolo[2,3-d]pyrimidine-7-carboxylic acid [3-(4-morpholin-4-yl-phenylcarbamoyl)-phenyl]-amide resin (50 mg, 0.05 mmol), prepared as in reference 1, in n-butanol (2 mL) is mixed with acetyl chloride (17.8 μL, 0.25 mmol) and 3-trifluoromethyl-aniline (31 μL, 0.25 mmol), or only mixed with HCl salt of 3-trifluoromethyl-aniline (50 mg, 0.25 mmol), and shaken at 80° C. for 24 hours. The resulting mixture is filtered and the resin is treated with TFA/CH$_2$Cl$_2$/H$_2$O (45/50/5) (600 μL) for 30 minutes before filtering and washing with CH$_2$Cl$_2$ (3×2 mL), MeOH (3×2 mL). The washes are then combined together and concentrated. The residue is purified by preparative HPLC to give 4-(3-trifluoromethyl-phenylamino)-pyrrolo[2,3-d]pyrimidine-7-carboxylic acid [3-(4-morpholin-4-yl-phenylcarbamoyl)-phenyl]-amide (19.0 mg, yield 64%). $^1$H NMR (400 MHz, DMSO-d$_6$) δ 11.75 (s, 1H), 10.16 (s, 1H), 10.09 (s, 1H), 8.69 (s, 1H), 8.31 (s, 1H), 8.22 (d, J=8.3 Hz, 1H), 8.15 (s, 1H), 7.94 (d, J=8.2 Hz, 1H), 7.92 (d, J=3.9 Hz, 1H), 7.77 (d, J=7.7 Hz, 1H), 7.64 (d, J=8.8 Hz, 2H), 7.63 (d, J=6.9 Hz, 1H), 7.58 (t, J=8.0 Hz, 1H), 7.44 (d, J=7.7 Hz, 1H), 7.13 (d, J=4.0 Hz, 1H), 6.95 (d, J=9.0 Hz, 2H), 3.74 (t, J=4.6 Hz, 4H), 3.08 (t, J=4.7 Hz, 4H); ESIMS m/z 602.20 (M$^+$+1).

Example 2

4-(4-Trifluoromethyl-1-phenylamino)-pyrrolo[2,3-d]pyrimidine-7-carboxylic acid {2-methyl-5-[4-(4-methyl-piperazin-1-ylmethyl)-benzoylamino]-phenyl}-amide

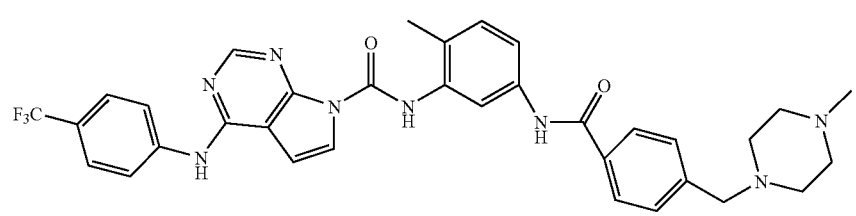

4-Chloro-pyrrolo[2,3-d]pyrimidine-7-carboxylic acid {2-methyl-5-[4-(4-methyl-piperazin-1-ylmethyl)-benzoylamino]-phenyl}-amide resin (50 mg, 0.05 mmol), prepared as in reference 2, in n-butanol (2 mL) is mixed with acetyl chloride (17.8 µL, 0.25 mmol) and 4-(trifluoromethyl) aniline (31 µL, 0.25 mmol), or only mixed with 4-trifluoromethyl-aniline hydrochloride (49.4 mg, 0.25 mmol) and shaken at 80° C. for 24 hours. The resulting mixture is filtered and the resin is treated with TFA/CH$_2$Cl$_2$/H$_2$O (45/50/5) (600 µL) for 30 minutes before filtering and washing with CH$_2$Cl$_2$ (3×2 mL), MeOH (3×2 mL). The washes are then combined together and concentrated. The residue is purified by preparative HPLC to give 4-(4-trifluoromethyl-1-phenylamino)-pyrrolo[2,3-d]pyrimidine-7-carboxylic acid {2-methyl-5-[4-(4-methyl-piperazin-1-ylmethyl)-benzoylamino]-phenyl}-amide (18.6 mg, yield 58%); $^1$H NMR (400 MHz, DMSO-d$_6$) δ 11.47 (s, 1H), 10.34 (s, 1H), 10.16 (s, 1H), 8.67 (s, 1H), 8.54 (s, 1H), 8.15 (d, J=8.5 Hz, 2H), 8.03 (d, J=8.0 Hz, 2H), 7.93 (d, J=3.9 Hz, 1H), 7.76 (d, J=8.6 Hz, 2H), 7.59 (d, J=8.0 Hz, 1H), 7.56 (d, J=8.0 Hz, 2H), 7.30 (d, J=8.0 Hz, 1H), 7.17 (d, J=3.9 Hz, 1H), 4.01 (s, 2H), 3.80-3.20 (m, 8H), 2.83 (s, 3H), 2.46 (s, 3H); ESIMS m/z 643.20 (M$^+$30 1).

chloride (52.3 mg, 0.25 mmol) or mixed with acetyl chloride (17.8 µL, 0.25 mmol) and aniline and shaken at 80° C. for 24 hours. The resulting mixture is filtered and the resin is treated with TFA/CH$_2$Cl$_2$/H$_2$O (45/50/5) (600 µL) for 30 minutes before filtering and washing with CH$_2$Cl$_2$ (3×2 mL), MeOH (3×2 mL). The washes are then combined together and concentrated. The residue is purified by preparative HPLC-MS to give 4-(3-dimethylamino-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide (23.2 mg, yield 71%); $^1$H NMR (400 MHz, DMSO-d$_6$) δ 11.60 (s, 1H), 10.65 (s, 1H), 9.68 (s, 1H), 9.61 (s, 1H), 8.60 (s, 1H), 8.54 (s, 1H), 8.53 (s, 1H), 8.46 (s, 1H), 8.41 (s, 1H), 8.16 (s, 1H), 7.82 (d, J=3.9 Hz, 1H), 7.60 (d, J=8.2 Hz, 1H), 7.32 (d, J=3.6 Hz, 1H), 6.54 (d, J=8.4 Hz, 1H), 2.92 (s, 6H), 2.45 (s, 3H), 2.35 (s, 3H); ESIMS m/z 654.2 (M$^+$+1).

Example 4

4-(3-Carbamoyl-phenylamino)-pyrrolo[2,3-d]pyrimidine-7-carboxylic acid {2-methyl-5-[4-(4-methyl-piperazin-1-ylmethyl)-benzoylamino]-phenyl}-amide

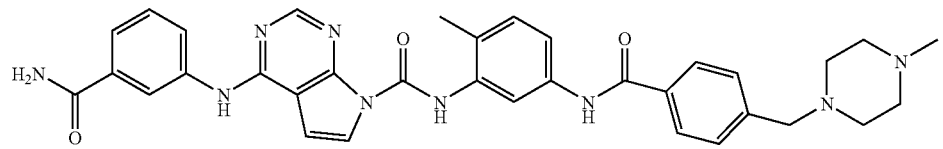

Example 3

4-(3-Dimethylamino-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide

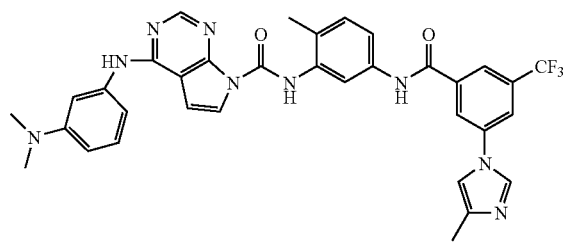

4-Chloro-pyrrolo[2,3-d]pyrimidine-7-carboxylic acid {2-methyl-5-[3-(4-methyl-imidazol-1-yl)-5-trifluoromethyl-benzoylamino]-phenyl}-amide resin (50 mg, 0.05 mmol), prepared as in reference 3, in n-butanol (2 mL) is mixed with N,N-dimethyl-1,3-phenylenediamine dihydro- 4-Chloro-pyrrolo[2,3-d]pyrimidine-7-carboxylic acid {2-methyl-5-[4-(4-methyl-piperazin-1-ylmethyl)-benzoylamino]-phenyl}-amide resin (50 mg, 0.05 mmol), prepared as in reference 2, in n-butanol (2 mL) is mixed with acetyl chloride (17.8 µL, 0.25 mmol) and 3-aminobenzamide (34 mg, 0.25 mmol), and shaken at 80° C. for 24 hours. The resulting mixture is filtered and the resin is treated with TFA/CH$_2$Cl$_2$/H$_2$O (45/50/5) (600 µL) for 30 minutes before filtering and washing with CH$_2$Cl$_2$ (3×2 mL), MeOH (3×2 mL). The washes are then combined together and concentrated. The residue is purified by preparative HPLC-MS to give 4-(3-carbamoyl-phenylamino)-pyrrolo[2,3-d]pyrimidine-7-carboxylic acid {2-methyl-5-[4-(4-methyl-piperazin-1-ylmethyl)-benzoylamino]-phenyl}-amide (18.5 mg, yield, 60%); $^1$H NMR (400 MHz, DMSO-d$_6$) δ 11.52 (s, 1H), 10.31 (s, 1H), 9.99 (s, 1H), 8.60 (s, 1H), 8.52 (d, J=1.71 Hz, 1H), 8.23 (s, 1H), 8.12 (d, J=7.59 Hz, 1H), 8.00 (s, 1H), 7.98 (d, J=8.02 Hz, 2H), 7.87 (d, J=3.89 Hz, 1H), 7.59 (dd, J=17.87, 9.00 Hz, 2H), 7.49 (d, J=7.98 Hz, 2H), 7.47 (s, 1H), 7.38 (s, 1H), 7.29 (d, J=8.48 Hz, 1H), 7.11 (d, J=3.89 Hz, 1H), 3.75 (s, 2H), 3.43-2.79 (m, 8H), 2.50 (s, 3H), 2.49 (s, 3H); ESIMS m/z 618.20 (M$^+$+1).

Example 5

4-(3-Sulfamoyl-phenylamino)-pyrrolo[2,3-d]pyrimidine-7-carboxylic acid {2-methyl-5-[4-(4-methyl-piperazin-1-ylmethyl)-benzoylamino]-phenyl}-amide

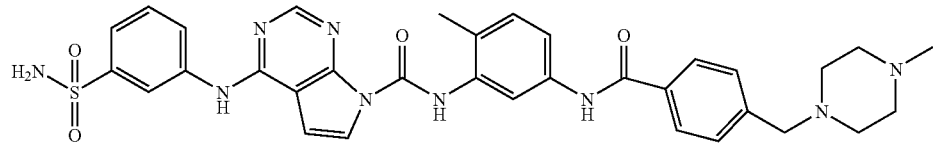

4-Chloro-pyrrolo[2,3-d]pyrimidine-7-carboxylic acid {2-methyl-5-[4-(4-methyl-piperazin-1-ylmethyl)-benzoylamino]-phenyl}-amide resin (50 mg, 0.05 mmol), prepared as in reference 2, in n-butanol (2 mL) is mixed with acetyl chloride (17.8 μL, 0.25 mmol) and 3-aminobenzenesulfonamide (43 mg, 0.25 mmol), and shaken at 80° C. for 24 hours. The resulting mixture is filtered and the resin is treated with TFA/CH$_2$Cl$_2$/H$_2$O (45/50/5) (600 μL) for 30 minutes before filtering and washing with CH$_2$Cl$_2$ (3×2 mL), MeOH (3×2 mL). The washes are then combined together with n-butanol and concentrated. The residue is purified by preparative HPLC-MS to give 4-(3-sulfamoyl-phenylamino)-pyrrolo[2,3-d]pyrimidine-7-carboxylic acid {2-methyl-5-[4-(4-methyl-piperazin-1-ylmethyl)-benzoylamino]-phenyl}-amide (18.0 mg, yield 55%); $^1$H NMR (400 MHz, DMSO-d$_6$) δ 11.45 (s, 1H), 10.27 (s, 1H), 10.09 (s, 1H), 8.59 (s, 1H), 8.49 (s, 1H), 8.29 (s, 1H), 8.17 (d, J=7.95 Hz, 1H), 7.95 (d, J=7.94, 2H), 7.87 (d, J=3.85 Hz, 1H), 7.54 (dd, J=7.61, 15.51 Hz, 2H), 7.52 (s, 1H), 7.45 (d, J=7.88 Hz, 2H), 7.37 (s, 2H), 7.25 (d, J=8.30 Hz, 1H), 7.11 (d, J=3.88 Hz, 1H), 3.69 (s, 2H), 3.54-3.3.17 (m, 2H), 3.01-2.93 (m, 6H), 2.75 (s, 3H), 2.41 (s, 3H); ESIMS m/z 654.20 (M$^+$+1).

Example 6

4-[3-(1-Hydroxy-ethyl)-phenylamino]-pyrrolo[2,3-d]pyrimidine-7-carboxylic acid {2-methyl-5-[3-(4-methyl-imidazol-1-yl)-5-trifluoromethyl-benzoylamino]-phenyl}-amide

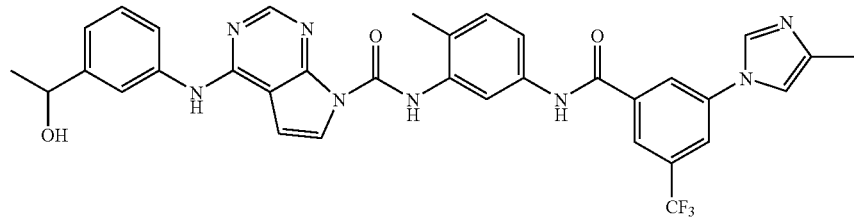

4-Chloro-pyrrolo[2,3-d]pyrimidine-7-carboxylic acid {2-methyl-5-[3-(4-methyl-imidazol-1-yl)-5-trifluoromethyl-benzoylamino]-phenyl}-amide resin (50 mg, 0.05 mmol), prepared as in reference 3, in n-butanol (2 mL) is mixed with acetyl chloride (17.8 μL, 0.25 mmol) and 3-(1-hydroxyethyl)aniline (34 mg, 0.25 mmol) and shaken at 80° C. for 24 hours. The resulting mixture is filtered and the resin is treated with TFA/CH$_2$Cl$_2$/H$_2$O (45/50/5) (600 μL) for 30 minutes before filtering and washing with CH$_2$Cl$_2$ (3×2 mL), MeOH (3×2 mL). The washes are then combined together with n-butanol and concentrated. The residue is purified by preparative HPLC-MS to give 4-[3-(1-hydroxyethyl)-phenylamino]-pyrrolo[2,3-d]pyrimidine-7-carboxylic acid {2-methyl-5-[3-(4-methyl-imidazol-1-yl)-5-trifluoromethyl-benzoylamino]-phenyl}-amide (16.6 mg, yield 51%); $^1$HNMR (400 MHz, DMSO-d$_6$) δ 11.60 (s, 1H), 10.68 (s, 1H), 9.85 (s, 1H), 9.62 (s, 1H), 8.62 (s, 1H), 8.57 (s, 1H), 8.54 (s, 1H), 8.47 (s, 1H), 8.43 (s, 1H), 8.17 (s, 1H), 7.85 (d, J=4.1 Hz, 2H), 7.70 (s, 1H), 7.61 (dd, J=6.5, 8.2 Hz, 1H), 7.35 (d, J=2.3 Hz, 1H), 7.33 (t, J=7.8 Hz, 1H), 7.09 (s, 1H), 7.08 (d, J=6.8 Hz, 1H), 4.75 (q, J=6.4 Hz, 1H), 2.47 (s, 3H), 2.36 (s, 3H), 1.36 (d, J=6.4 Hz, 3H); ESIMS m/z 655.2 (M$^+$+1).

Example 7

4-(3-Carbamoyl-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide

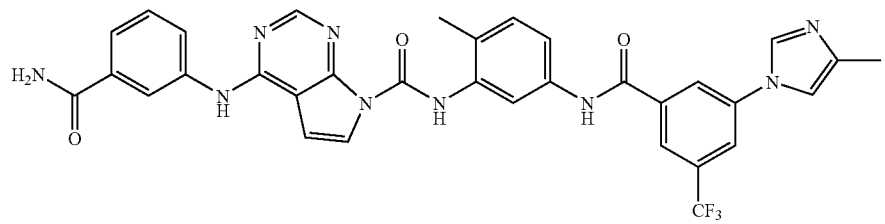

4-Chloro-pyrrolo[2,3-d]pyrimidine-7-carboxylic acid {2-methyl-5-[3-(4-methyl-imidazol-1-yl)-5-trifluoromethyl-benzoylamino]-phenyl}-amide, (50 mg, 0.09 mmol), prepared as in reference 3, in glacial acetic acid (2 mL) is mixed with 3-aminobenzamide (24.5 mg, 0.18 mmol) and shaken at 80° C. for 24 hours. The resulting mixture is directly purified by preparative HPLC-MS to give 4-(3-carbamoyl-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide (42.9 mg, yield 73%); $^1$H NMR (400 MHz, DMSO-$d_6$) δ 11.54 (s, 1H), 10.65 (s, 1H), 9.96 (s, 1H), 9.68 (s, 1H), 8.59 (d, J=13.1 Hz, 1H), 8.51 (s, 1H), 8.50 (s, 1H), 8.45 (s, 1H), 8.41 (s, 1H), 8.19 (d, J=10.1 Hz, 2H), 8.09 (d, J=7.9 Hz, 1H), 7.94 (s, 1H), 7.83 (d, J=3.9 Hz, 1H), 7.58 (d, J=8.2 Hz, 1H), 7.57 (d, J=4.7 Hz, 1H), 7.43 (t, J=7.9 Hz, 1H), 7.35 (s, 1H), 7.30 (d, J=8.5 Hz, 1H), 7.08 (d, J=3.9 Hz, 1H), 2.43 (s, 3H), 2.34 (s, 3H); ESIMS m/z 654.1 (M$^+$+1).

Example 8

4-(3-Sulfamoyl-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide 4-Chloro-pyrrolo[2,3-d]pyrimidine-7-carboxylic acid {2-methyl-5-[3-(4-methyl-imidazol-1-yl)-5-trifluoromethyl-benzoylamino]-phenyl}-amide, (50 mg, 0.09 mmol), prepared as in reference 3, in glacial acetic acid (2 mL) is mixed with 3-aminobenzenesulfonamide (31 mg, 0.18 mmol) and shaken at 80° C. for 24 hours. The resulting mixture is directly purified by preparative HPLC-MS to give 4-(3-sulfamoyl-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide (35.3 mg, yield 57%); $^1$H NMR (400 MHz, DMSO-$d_6$) δ 11.51 (s, 1H), 10.64 (s, 1H), 10.10 (s, 1H), 9.58 (s, 1H), 8.60 (s, 1H), 8.58 (s, 1H), 8.51 (s, 1H), 8.50 (s, 1H), 8.29 (s, 1H), 8.17 (d, J=8.1 Hz, 1H), 8.14 (s, 1H), 7.87 (d, J=3.9 Hz, 1H), 7.59 (d, J=1.8 Hz, 1H), 7.57 (d, J=7.6 Hz, 1H), 7.53 (d, 5.9 Hz, 1H), 7.37 (s, 2H), 7.30 (d, J=8.5 Hz, 1H), 7.11 (d, J=3.9 Hz, 1H), 2.44 (s, 3H), 2.33 (s, 3H); ESIMS m/z 690.1 (M$^+$+1).

By repeating the procedures described in the above examples, using appropriate starting materials, the following compounds of Formula I, as identified in Table 1, are obtained.

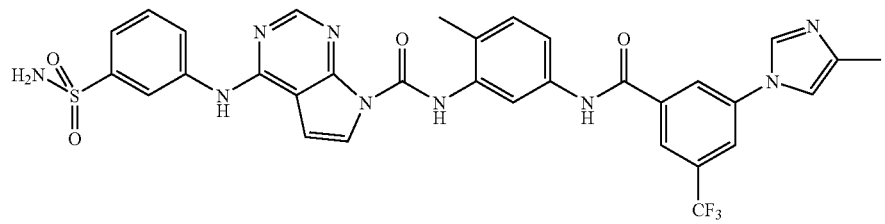

TABLE 1

| Compound Number | Structure | Physical Data $^1$H NMR 400 MHz (DMSO-$d_6$) and/or MS (m/z) |
|---|---|---|
| 9 | 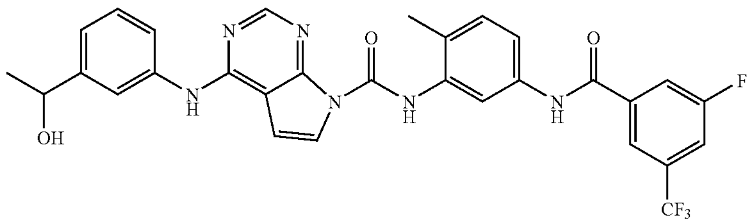 | $^1$H NMR (400 MHz, DMSO-$d_6$) δ 11.58(s, 1H), 10.59(s, 1H), 9.84(s, 1H), 8.57(s, 1H), 8.53 (s, 1H), 8.20(s, 1H), 8.15(d, J=9.2 Hz, 1H), 7.97d, J=8.2 Hz, 1H), 7.86(d, J=4.2 Hz, 2H), 7.70(s, 1H), 7.60(d, J=8.2 Hz, 1H), 7.35(s, 1H), 7.32(d, J=8.0 Hz, 1H), 7.1(d, J=6.7 Hz, 2H), 4.75(q, J=6.1 Hz, 1H), 2.46(s, 3H), 1.36(d, J=6.4 Hz, 3H); ESIMS m/z 593.10 (M$^+$ + 1). |
| 10 | 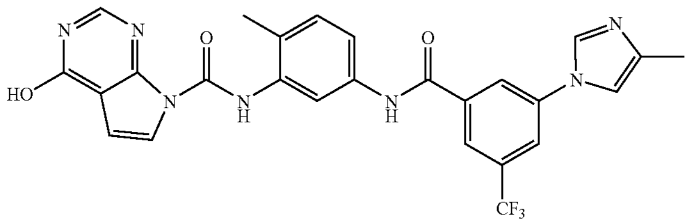 | $^1$H NMR (400 MHz, DMSO-$d_6$) δ 11.19(s, 1H), 10.66(s, 1H), 9.36(s, 1H), 9.36(s, 1H), 8.51 (s, 1H), 8.44(s, 1H), 8.43(s, 1H), 8.38(s, 1H), 8.34(s, 1H), 8.27(s, 1H), 7.98(s, 1H), 7.68 (d, J=3.9 Hz, 1H), 7.51(s, J=1.9 Hz, 1H), 7.31(d, J=8.4 Hz, 1H), 6.73(d, J=3.9 Hz, 1H), 2.38(s, 3H), 2.32(s, 3H); ESIMS m/z 536.10 (M$^+$ + 1). |
| 11 | 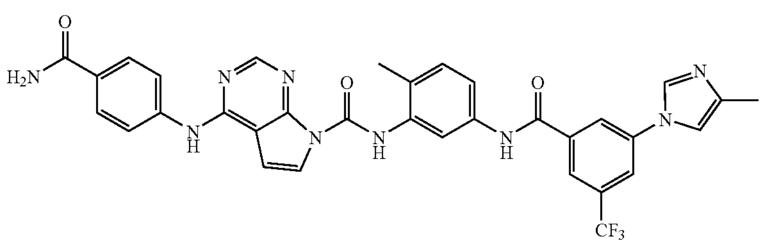 | $^1$H NMR (400 MHz, DMSO-$d_6$) δ 11.56(s, 1H), 10.67(s, 1H), 10.03(s, 1H), 9.55(s, 1H), 8.66 (s, 1H), 8.61(s, 1H), 8.55(d, J=1.8 Hz, 1H), 8.46(s, 1H), 8.42 (s, 1H), 8.16(s, 1H), 7.98(s, 1H), 7.96(s, 1H), 7.92(s, 1H), 7.91(s, 1H), 7.90(d, J=4.7 Hz, 1H), 7.64(dd, J=1.8, 8.2 Hz, 1H), 7.35(d, J=8.5 Hz, 1H), 7.27(s, 1H), 7.16(d, J=4.0 Hz, 1H), 2.48(s, 3H), 2.35(s, 3H); ESIMS m/z 654.15 (M$^+$ + 1). |
| 12 | 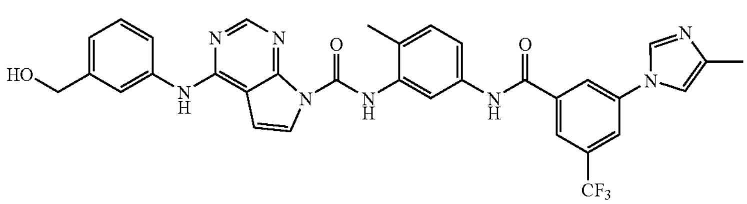 | $^1$H NMR (400 MHz, DMSO-$d_6$) δ 11.60(s, 1H), 10.66(s, 1H), 9.84(s, 1H), 9.44(s, 1H), 8.59(s, 1H), 8.58(s, 1H), 8.55(s, 1H), 8.43 (s, 1H), 8.40(s, 1H), 8.11(s, 1H), 7.85(d, J=4.0 Hz, 1H), 7.80(d, J=8.3 Hz, 1H), 7.74(s, 1H), 7.63(d, J=8.1 Hz, 1H), 7.35(d, J=6.3 Hz, 1H), 7.33(d, J=7.8 Hz, 1H), 7.09 (dd, J=3.9 Hz, 1H), 7.06(d, J=7.5 Hz, 1H), 4.54(s, 2H), 2.47(s, 3H), 2.34(s, 3H); ESIMS m/z 641.10 (M$^+$ + 1). |
| 13 | 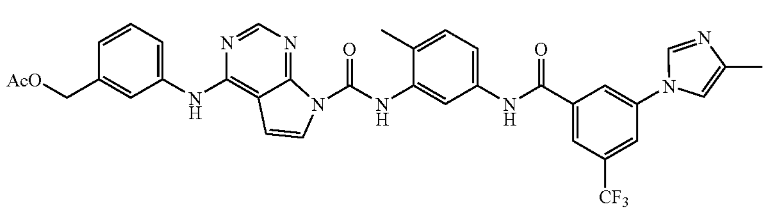 | $^1$H NMR (400 MHz, DMSO-$d_6$) δ 11.59(s, 1H), 10.66(s, 1H), 9.90(s, 1H), 9.42(s, 1H), 8.59 (s, 2H), 8.55(s, 1H), 8.43(s, 1H), 8.40(s, 1H), 8.11(s, 1H), 7.91(s, 1H), 7.87(d, J=4.0 Hz, 1H), 7.79(s, 1H), 7.63(d, J=8.0 Hz, 1H), 7.40(t, J=7.9 Hz, 1H), 7.35(d, J=8.4 Hz, 1H), 7.12(s, 1H), 7.11(d, J=3.5 Hz, 1H), 5.12(s, 2H), 2.47(s, 3H), 2.34(s, 3H), 2.10(s, 3H); ESIMS m/z 683.15 (M$^+$ + 1). |

TABLE 1-continued

| Compound Number | Structure | Physical Data<br>¹H NMR 400 MHz (DMSO-d₆) and/or MS (m/z) |
|---|---|---|
| 14 | 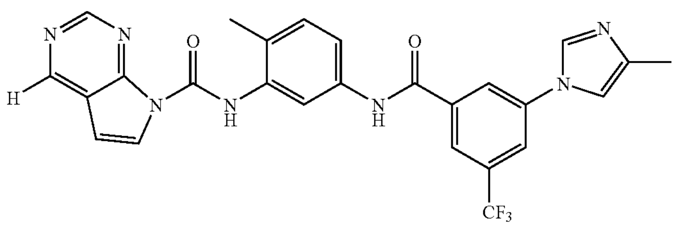 | ¹H NMR (400 MHz, DMSO-d₆) δ 11.22(s, 1H), 10.66(s, 1H), 9.51(s, 1H), 9.24(s, 1H), 9.11 (s, 1H), 8.59(s, 1H), 8.53(s, 1H), 8.44(s, 1H), 8.40(s, 1H), 8.13(s, 1H), 8.12(s, 1H), 7.62 (d, J=10.1 Hz, 1H), 7.35(d, J= 8.3 Hz, 1H), 6.94(d, J=3.9 Hz, 1H), 2.48(s, 3H), 2.33(s, 3H); ESIMS m/z 520.10 (M⁺ + 1). |
| 15 | 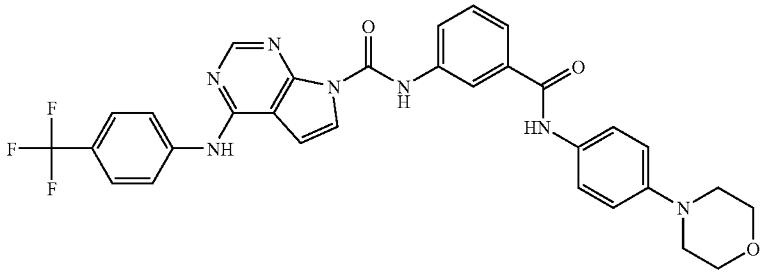 | ESIMS m/z 602.15 (M⁺ + 1). |
| 16 | 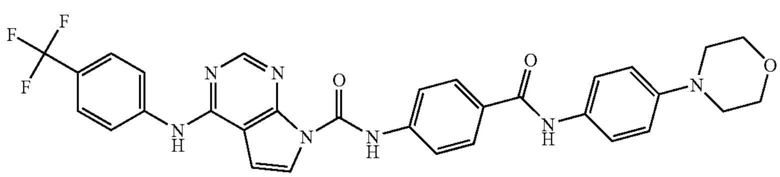 | ESIMS m/z 602.20 (M⁺ + 1). |
| 17 | 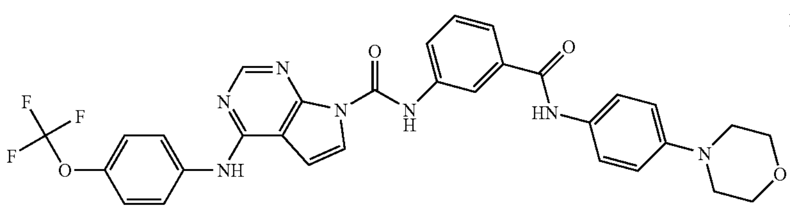 | ESIMS m/z 618.20 (M⁺ + 1). |
| 18 | 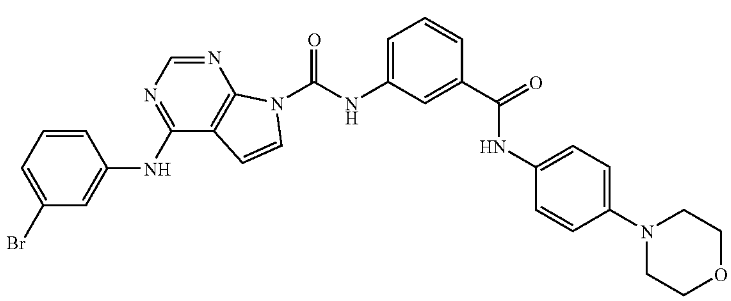 | ESIMS m/z 612.20 (M⁺ + 1), 614.20 (M⁺ + 3). |
| 19 | 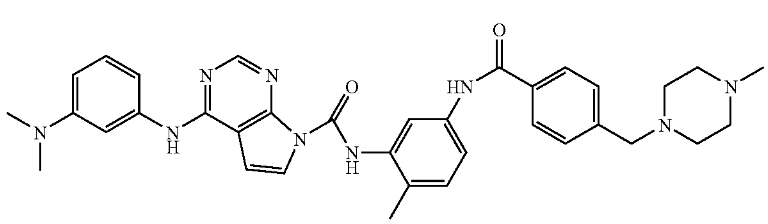 | ESIMS m/z 618.30 (M⁺ + 1). |

TABLE 1-continued

| Compound Number | Structure | Physical Data ¹H NMR 400 MHz (DMSO-d$_6$) and/or MS (m/z) |
|---|---|---|
| 20 | 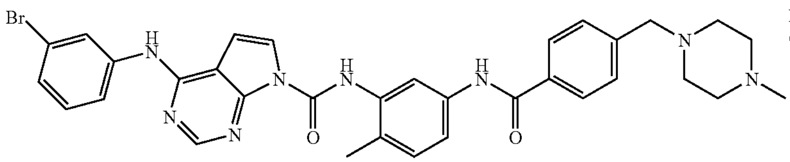 | ESIMS m/z 653.20 (M$^+$ + 1), 655.20 (M$^+$ + 3). |
| 21 | 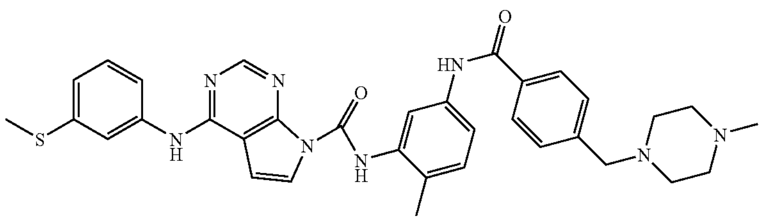 | ESIMS m/z 621.20 (M$^+$ + 1). |
| 22 | 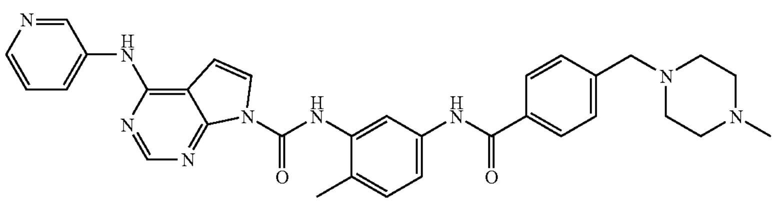 | ESIMS m/z 576.20 (M$^+$ + 1). |
| 23 | 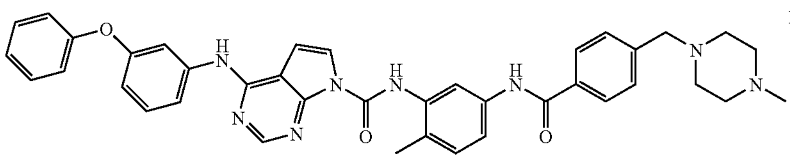 | ESIMS m/z 667.30 (M$^+$ + 1). |
| 24 | 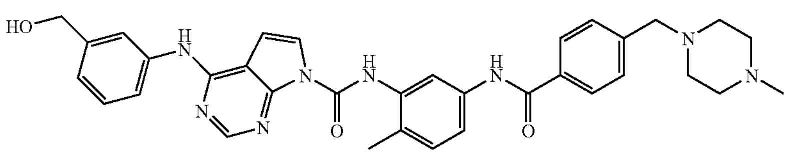 | ESIMS m/z 605.20 (M$^+$ + 1). |
| 25 | 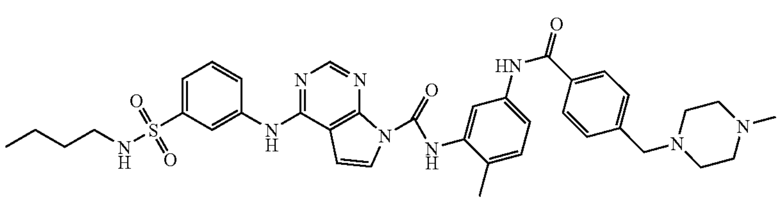 | ESIMS m/z 710.30 (M$^+$ + 1). |
| 26 | 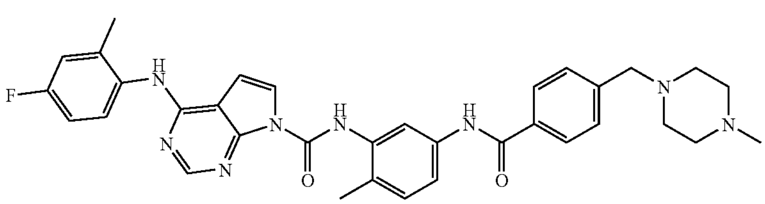 | ESIMS m/z 607.20 (M$^+$ + 1). |
| 27 | 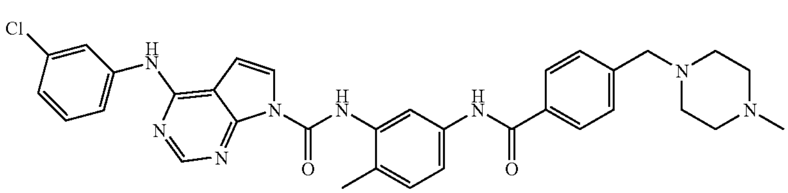 | ESIMS m/z 609.20 (M$^+$ + 1). |

TABLE 1-continued

| Compound Number | Structure | Physical Data<br>¹H NMR 400 MHz (DMSO-$d_6$)<br>and/or MS (m/z) |
|---|---|---|
| 28 | 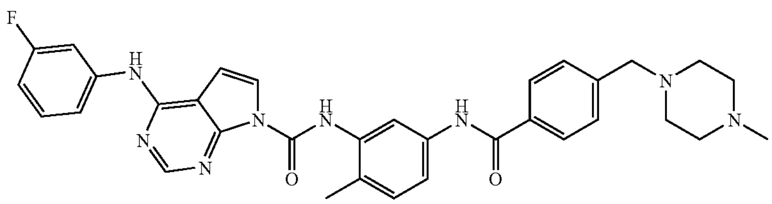 | ESIMS m/z 593.20 (M⁺ + 1). |
| 29 | 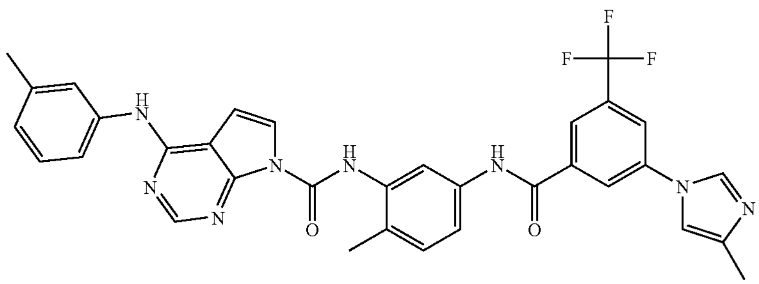 | ESIMS m/z 625.20 (M⁺ + 1). |
| 30 | 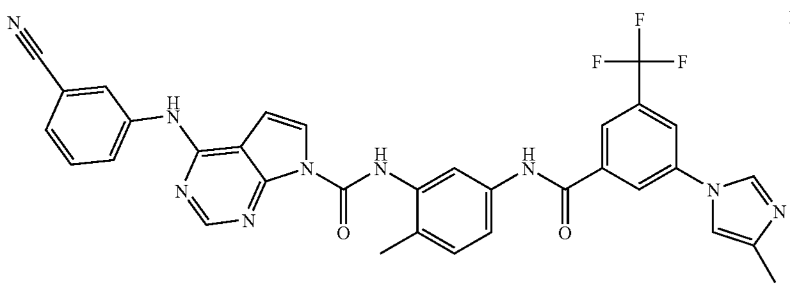 | ESIMS m/z 636.20 (M⁺ + 1). |
| 31 | 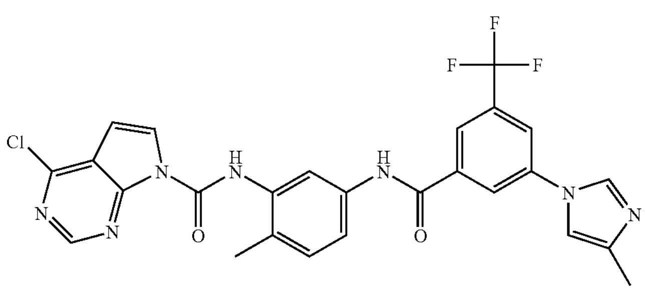 | ESIMS m/z 554.10 (M⁺ + 1). |
| 32 | 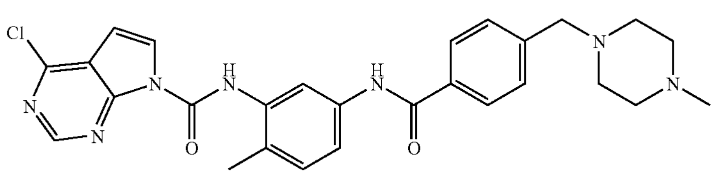 | ESIMS m/z 518.10 (M⁺ + 1). |
| 33 | 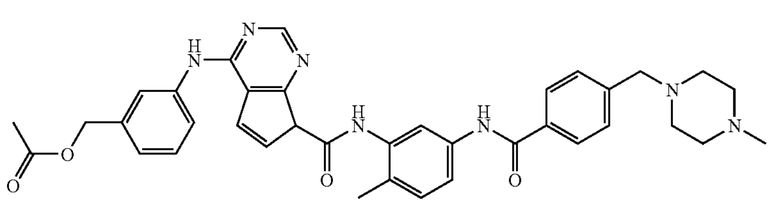 | ESIMS m/z 646.30 (M⁺ + 1). |

TABLE 1-continued
| Compound Number | Structure | Physical Data ¹H NMR 400 MHz (DMSO-$d_6$) and/or MS (m/z) |
|---|---|---|
| 34 | 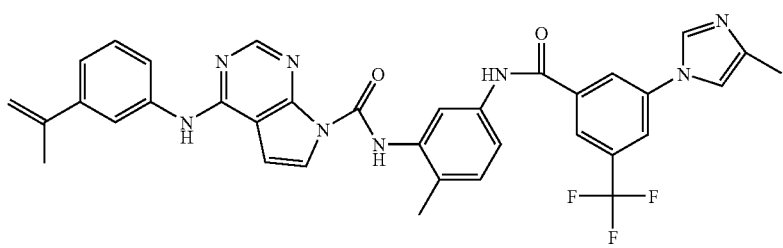 | ESIMS m/z 651.20 ($M^+$ + 1). |
| 35 | 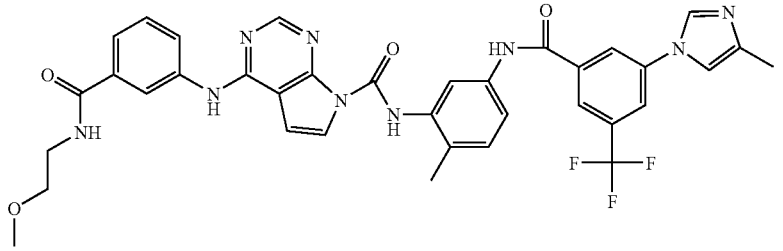 | ESIMS m/z 712.20 ($M^+$ + 1). |
| 36 | 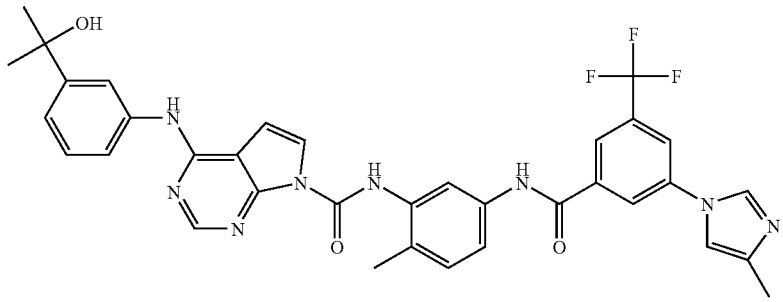 | ESIMS m/z 712.20 ($M^+$ + 1). |
| 37 | 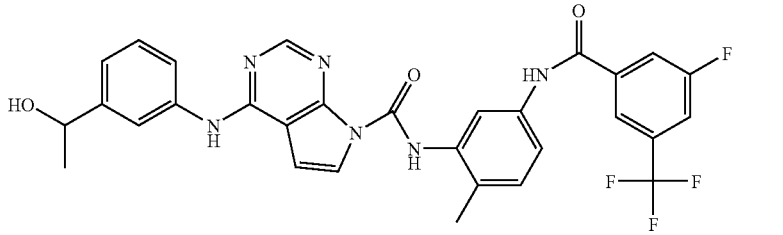 | ESIMS m/z 593.20 ($M^+$ + 1). |
| 38 | 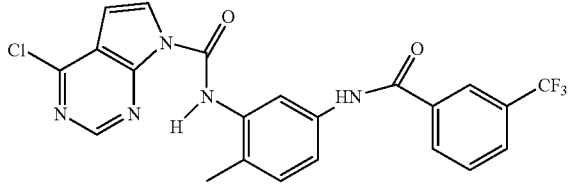 | ESIMS m/z 474.10 ($M^+$ + 1). |
| 39 | 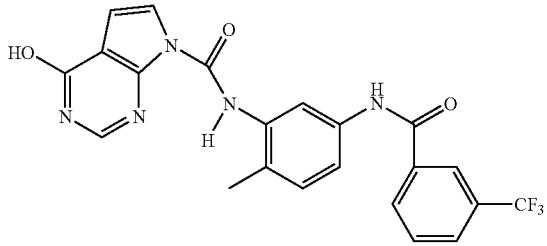 | ESIMS m/z 456.10 ($M^+$ + 1). |

TABLE 1-continued

| Compound Number | Structure | Physical Data $^1$H NMR 400 MHz (DMSO-$d_6$) and/or MS (m/z) |
|---|---|---|
| 40 | 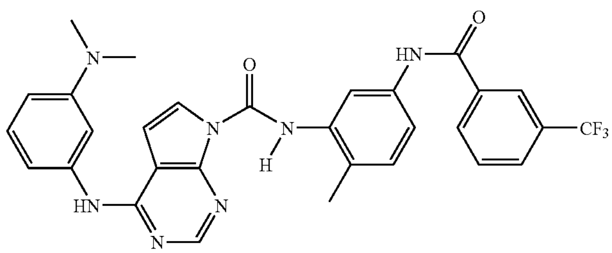 | ESIMS m/z 574.20 (M$^+$ + 1). |
| 41 | 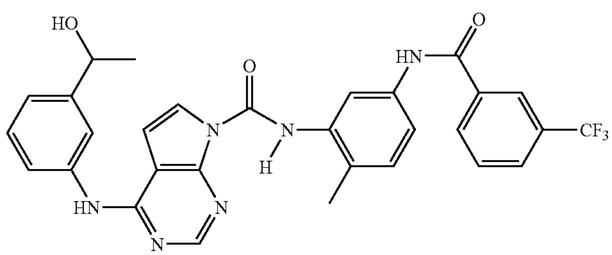 | ESIMS m/z 575.20 (M$^+$ + 1). |
| 42 | 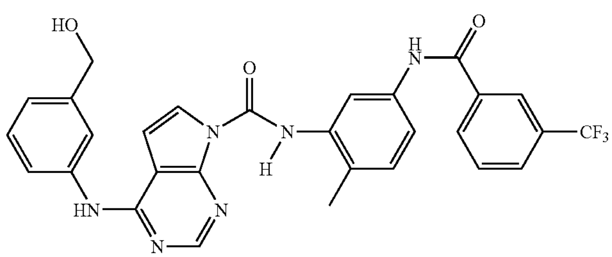 | ESIMS m/z 561.20 (M$^+$ + 1). |
| 43 | 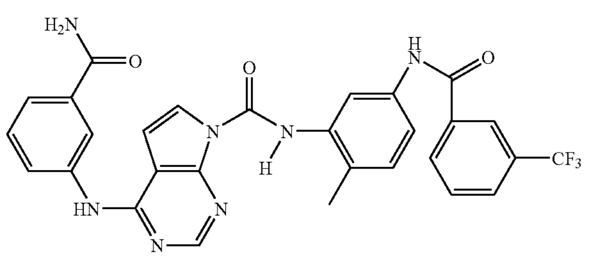 | ESIMS m/z 574.20 (M$^+$ + 1). |
| 44 | 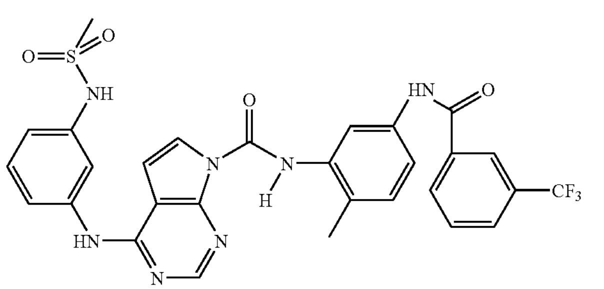 | ESIMS m/z 624.20 (M$^+$ + 1). |

TABLE 1-continued

| Compound Number | Structure | Physical Data<br>¹H NMR 400 MHz (DMSO-d₆)<br>and/or MS (m/z) |
|---|---|---|
| 45 | 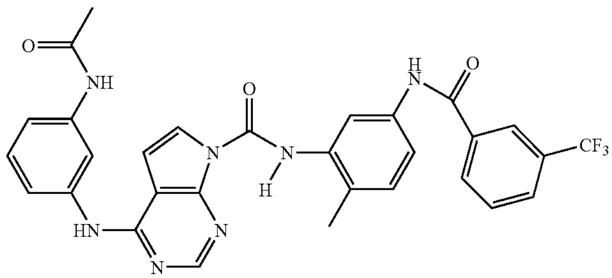 | ESIMS m/z 588.20 (M⁺ + 1). |
| 46 | 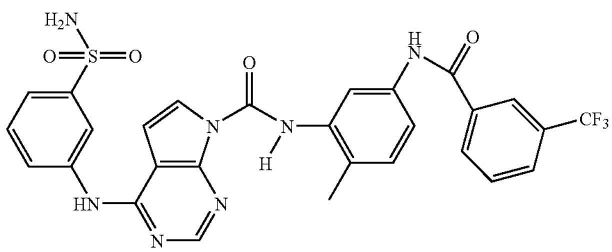 | ESIMS m/z 610.10 (M⁺ + 1). |
| 47 | 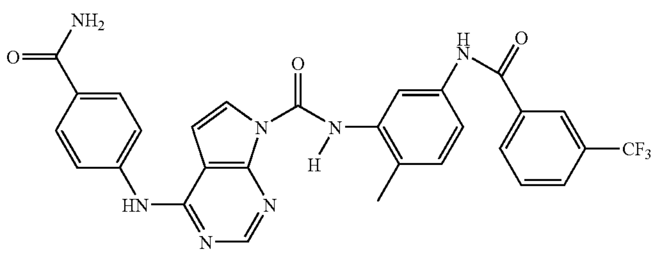 | ESIMS m/z 574.20 (M⁺ + 1). |
| 48 | 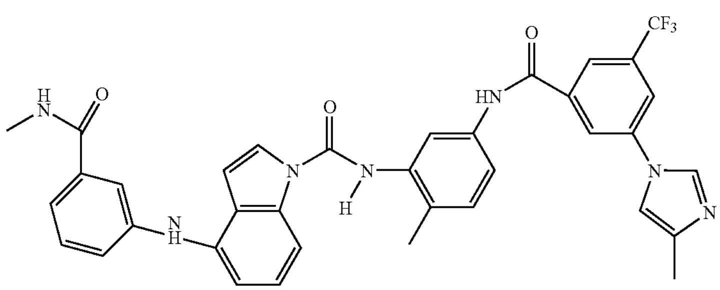 | ESIMS m/z 668.20 (M⁺ + 1). |
| 49 | 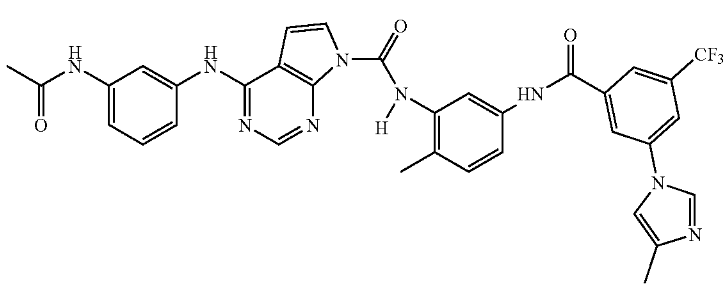 | ESIMS m/z 668.20 (M⁺ + 1). |

TABLE 1-continued
| Compound Number | Structure | Physical Data ¹H NMR 400 MHz (DMSO-$d_6$) and/or MS (m/z) |
|---|---|---|
| 50 | 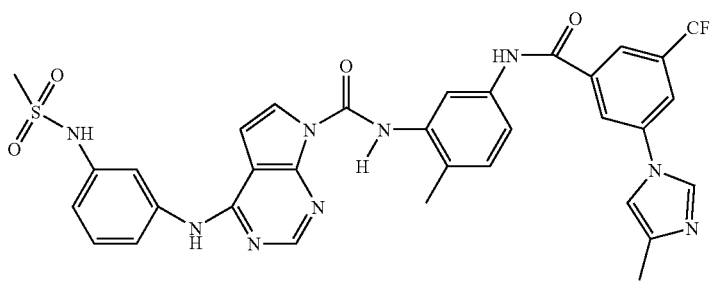 | ESIMS m/z 704.2 ($M^+$ + 1). |
| 51 | 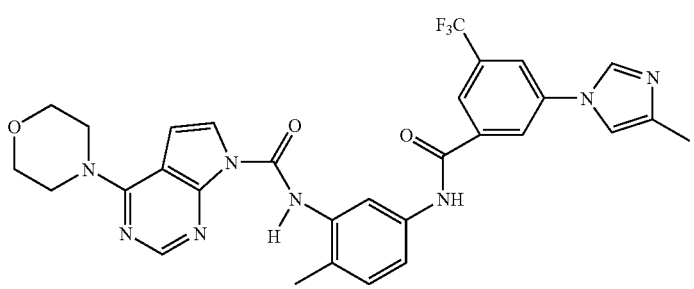 | ESIMS m/z 605.2 ($M^+$ + 1). |
| 52 | 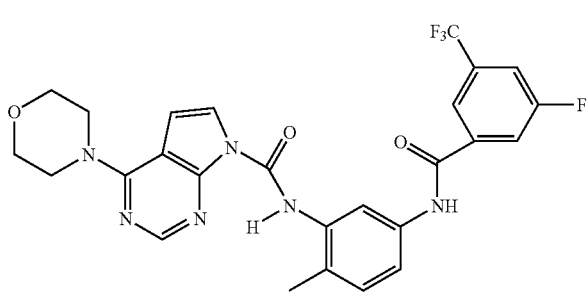 | ESIMS m/z 543.20 ($M^+$ + 1). |
| 53 | 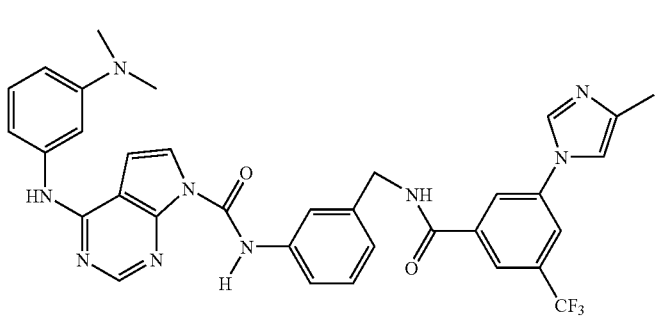 | ESIMS m/z 654.20 ($M^+$ + 1). |
| 54 | 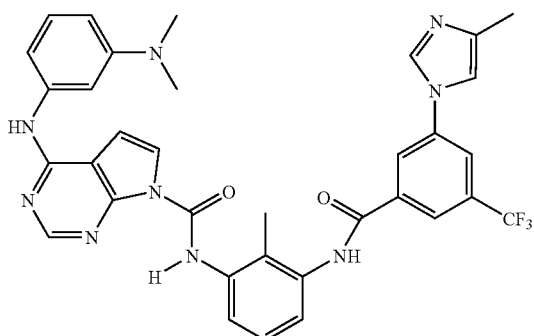 | ESIMS m/z 654.20 ($M^+$ + 1). |

ASSAYS

Compounds of the present invention are assayed to measure their capacity to selectively inhibit cell proliferation of 32D cells expressing BCR-Abl (32D-p210) compared with parental 32D cells. Compounds selectively inhibiting the proliferation of these BCR-Abl transformed cells are tested for anti-proliferative activity on Ba/F3 cells expressing either wild type or the mutant forms of BCR-Abl. In addition, compounds are assayed to measure their capacity to inhibit B-RAF.

Inhibition of Cellular BCR-Abl Dependent Proliferation (High Throughput Method)

The murine cell line used is the 32D hemopoietic progenitor cell line transformed with BCR-Abl cDNA (32D-p210). These cells are maintained in RPMI/10% fetal calf serum (RPMI/FCS) supplemented with penicillin 50 μg/mL, streptomycin 50 μg/mL and L-glutamine 200 mM. Untransformed 32D cells are similarly maintained with the addition of 15% of WEHI conditioned medium as a source of IL3.

50 μl of a 32D or 32D-p210 cells suspension are plated in Greiner 384 well microplates (black) at a density of 5000 cells per well. 50 nL of test compound (1 mM in DMSO stock solution) is added to each well (STI571 is included as a positive control). The cells are incubated for 72 hours at 37° C., 5% $CO_2$. 10 μL of a 60% Alamar Blue solution (Tek diagnostics) is added to each well and the cells are incubated for an additional 24 hours. The fluorescence intensity (Excitation at 530 nm, Emission at 580 nm) is quantified using the Acquest™ system (Molecular Devices).

Inhibition of Cellular BCR-Abl Dependent Proliferation 32D-p210 cells are plated into 96 well TC plates at a density of 15,000 cells per well. 50 μL of two fold serial dilutions of the test compound ($C_{max}$ is 40 μM) are added to each well (STI571 is included as a positive control). After incubating the cells for 48 hours at 37° C., 5% $CO_2$, 15 μL of MTT (Promega) is added to each well and the cells are incubated for an additional 5 hours. The optical density at 570 nm is quantified spectrophotometrically and $IC_{50}$ values, the concentration of compound required for 50% inhibition, determined from a dose response curve.

Effect on Cell Cycle Distribution 32D and 32D-p210 cells are plated into 6 well TC plates at $2.5 \times 10^6$ cells per well in 5 mL of medium and test compound at 1 or 10 μM is added (STI571 is included as a control). The cells are then incubated for 24 or 48 hours at 37° C., 5% $CO_2$. 2 ml of cell suspension is washed with PBS, fixed in 70% EtOH for 1 hour and treated with PBS/EDTA/RNase A for 30 minutes. Propidium iodide (Cf=10 μg/ml) is added and the fluorescence intensity is quantified by flow cytometry on the FACScalibur™ system (BD Biosciences). Test compounds of the present invention demonstrate an apoptotic effect on the 32D-p210 cells but do not induce apoptosis in the 32D parental cells.

Effect on Cellular BCR-Abl Autophosphorylation

BCR-Abl autophosphorylation is quantified with capture Elisa using a c-abl specific capture antibody and an antiphosphotyrosine antibody. 32D-p210 cells are plated in 96 well TC plates at $2 \times 10^5$ cells per well in 50 μL of medium. 50 μL of two fold serial dilutions of test compounds ($C_{max}$ is 10 μM) are added to each well (STI571 is included as a positive control). The cells are incubated for 90 minutes at 37° C., 5% $CO_2$. The cells are then treated for 1 hour on ice with 150 μL of lysis buffer (50 mM Tris-HCl, pH 7.4, 150 mM NaCl, 5 mM EDTA, 1 mM EGTA and 1% NP-40) containing protease and phosphatase inhibitors. 50 μL of cell lysate is added to 96 well optiplates previously coated with anti-abl specific antibody and blocked. The plates are incubated for 4 hours at 4° C. After washing with TBS-Tween 20 buffer, 50 μL of alkaline-phosphatase conjugated anti-phosphotyrosine antibody is added and the plate is further incubated overnight at 4° C. After washing with TBS-Tween 20 buffer, 90 μL of a luminescent substrate are added and the luminescence is quantified using the Acquest™ system (Molecular Devices). Test compounds of the invention that inhibit the proliferation of the BCR-Abl expressing cells, inhibit the cellular BCR-Abl autophosphorylation in a dose-dependent manner.

Effect on Proliferation of Cells Expressing Mutant Forms of BCR-Abl

Compounds of the invention are tested for their antiproliferative effect on Ba/F3 cells expressing either wild type or the mutant forms of BCR-Abl (G250E, E255V, T315I, F317L, M351T) that confers resistance or diminished sensitivity to STI571. The antiproliferative effect of these compounds on the mutant-BCR-Abl expressing cells and on the non transformed cells were tested at 10, 3.3, 1.1 and 0.37 μM as described above (in media lacking IL3). The $IC_{50}$ values of the compounds lacking toxicity on the untransformed cells were determined from the dose response curves obtained as describe above.

B-RAF

Compounds of the invention are tested for their ability to inhibit the activity of B-RAF. The assay is carried out in 384-well MaxiSorp plates (NUNC) with black walls and clear bottom. The substrate, IκBα is diluted in DPBS (1:750) and 15 μL is added to each well. The plates are incubated at 4° C. overnight and washed 3 times with TBST (25 mM Tris, pH 8.0, 150 mM NaCl and 0.05% Tween-20) using the EMBLA plate washer. Plates are blocked by Superblock (15 μL/well) for 3 hours at room temperature, washed 3 times with TBST and pat-dried. Assay buffer containing 20 μM ATP (10 μL) is added to each well followed by 100 nL or 500 nL of compound. B-RAF is diluted in the assay buffer (1 μL into 25 μl) and 10 μL of diluted B-RAF is added to each well (0.4 μg/well). The plates are incubated at room temperature for 2.5 hours. The kinase reaction is stopped by washing the plates 6 times with TBST. Phosph-IκBα (Ser32/36) antibody is diluted in Superblock (1:10,000) and 15 μL is added to each well. The plates are incubated at 4° C. overnight and washed 6 times with TBST. AP-conjugated goat-anti-mouse IgG is diluted in Superblock (1:1,500) and 15 μL is added to each well. Plates are incubated at room temperature for 1 hour and washed 6 times with TBST. 15 μL of Attophos AP substrate is added to each well and plates are incubated at room temperature for 15 minutes. Plates are read on Acquest or Analyst GT using a Fluorescence Intensity Nanxin BBT anion (505 dichroic mirror).

Upstate KinaseProfiler™—Radio-enzymatic filter binding assay

Compounds of the invention are assessed for their ability to inhibit individual members of a panel of kinases (a partial, non-limiting list of kinases includes: BMX, CSK, TrkB, FGFR3, Fes, Lck, B-RAF, C-RAF, MKK6, SAPK2α and SAPK2β). The compounds are tested in duplicates at a final concentration of 10 μM following this generic protocol. Note that the kinase buffer composition and the substrates vary for the different kinases included in the "Upstate KinaseProfiler™" panel. The compounds are tested in duplicates at a final concentration of 10 μM following this generic protocol. Note that the kinase buffer composition and the substrates vary for the different kinases included in the "Upstate KinaseProfiler™" panel. Kinase buffer (2.5 μL, 10×—containing $MnCl_2$ when required), active kinase (0.001-0.01 Units; 2.5 μL), specific or Poly(Glu4-Tyr) peptide (5-500 μM or 0.01 mg/ml) in kinase buffer and kinase buffer (50 μM; 5 μL) are mixed in an eppendorf on ice. A Mg/ATP mix (10 μL; 67.5 (or 33.75) mM $MgCl_2$, 450 (or 225) μM ATP and 1 μCi/μl [γ-$^{32}$P]-ATP (3000 Ci/mmol)) is added and the reaction is incubated at about 30° C. for about 10 minutes. The reaction mixture is spotted (20 μL) onto a 2 cm×2 cm P81 (phosphocellulose, for positively charged peptide substrates) or Whatman No. 1 (for Poly (Glu4-Tyr) peptide substrate) paper square. The assay squares are washed 4 times, for 5 minutes each, with 0.75% phosphoric acid and washed once with acetone for 5 minutes. The assay squares are transferred to a scintillation vial, 5 ml scintillation cocktail are added and $^{32}$P incorporation (cpm) to the peptide substrate is quantified with a Beckman scintillation counter. Percentage inhibition is calculated for each reaction.

Compounds of Formula I, in free form or in pharmaceutically acceptable salt form, exhibit valuable pharmacological properties, for example, as indicated by the in vitro tests described in this application. For example, compounds of Formula I preferably show an $IC_{50}$ in the range of $1×10^{-10}$ to $1×10^{-5}$ M, preferably less than 100 nM for wild type BCR-Abl and G250E, E255V, T315I, F317L and M351T BCR-Abl mutants.

For example: 4-(3-carbamoyl-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide (Example 7) has an $IC_{50}$ of 5 nM, 47 nM, 31 nM, 115 nM 9 nM and 5 nM for wild type, G250E, E255V, T315I, F317L and M351T BCR-Abl, respectively. At a concentration of 10 μM, the compound inhibits the activity of Abl, BCR-Abl, Bmx, CSK, TrkB, FGFR3, Fes, Lck, B-RAF, C-RAF, MKK6, SAPK2α and SAPK2β kinases by greater than 50%, preferably greater than 75%. For example, 4-(3-carbamoyl-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide (Example 7) shows a percentage inhibition of: Bmx (100%), c-Raf (99%), CSK (100%), Fes (98%), FGFR3 (95%), Lck (96%), MKK6 (98%), SAPK2α (100%), SAPK2β (100%) and TrkB (98%);

4-(3-Dimethylamino-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide (Example 3) has an $IC_{50}$ of 22 nM, 170 nM, 220 nM, 370 nM, 50 nM and 29 nM for wild type, G250E, E255V, T315I, F317L and M351T BCR-Abl, respectively. The compound has an $IC_{50}$ of 32 nM for B-Raf. At a concentration of 10 μM, the compound shows a percentage inhibition of: Bmx (100%), c-Raf (83%), CSK (90%), Fes (82%), Lck (95%), SAPK2β(95%) and TrkB (100%).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:
1. A compound of formula I:

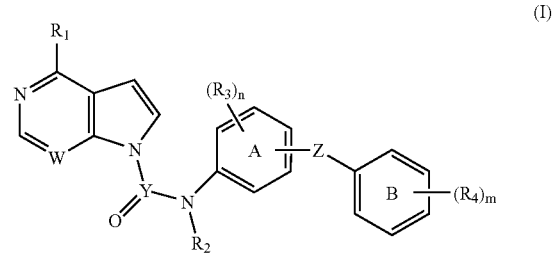

in which:

W is N;

Y is selected from C, S and S(O);

Z is a divalent radical selected from —Y(O)NR$_5$— and —NR$_5$Y(O)—; wherein Y is selected from C, S and S(O); and R$_5$ is selected from hydrogen and C$_{1-12}$alkyl;

R$_1$ is selected from hydrogen, halo, hydroxy C$_{1-6}$alkyl, C$_{1-6}$alkoxy and —NR$_6$R$_7$; wherein R$_6$ is selected from hydrogen and C$_{1-6}$alkyl; R$_7$ is selected from C$_{6-10}$aryl, C$_{5-10}$heteroaryl, C$_{3-12}$cycloalkyl and C$_{3-8}$heterocycloalkyl; or R$_6$ and R$_7$ together with the nitrogen to which both R$_6$ and R$_7$ are attached form C$_{3-8}$heterocycloalkyl or C$_{5-10}$heteroaryl; wherein any aryl, heteroaryl, cycloalkyl or heterocycloalkyl of R$_7$ or of the combination of R$_6$ and R$_7$ can be optionally substituted with 1 to 3 radicals selected from halo, cyano, nitro, C$_{1-6}$alkyl, C$_{2-6}$alkenyl, C$_{2-6}$alkynyl, halo-substituted-C$_{1-6}$alkyl, C$_{1-6}$alkoxy, halo-substituted-C$_{1-6}$alkoxy, —XNR$_8$R$_8$, —XC(O)NR$_8$R$_8$, —XC(O)NR$_8$XOR$_8$, —XS(O)$_{0-2}$NR$_8$R$_8$, —XS(O)$_{0-2}$R$_8$, —XNR$_8$S(O)$_{0-2}$R$_8$, —XNR$_8$C(O)R$_8$, —XNR$_8$SR$_8$, —XP(O)NR$_8$R$_8$, —XCR$^8$(OR$_8$)R$_8$, —XOC(O)R$_8$, —XOR$_8$ and —XOR$_9$; wherein X is a bond or C$_{1-12}$alkylene, R$_8$ is independently selected from hydrogen and C$_{1-6}$alkyl, R$_9$ is selected from C$_{6-10}$aryl and C$_{5-10}$heteroaryl;

R$_2$ is selected from hydrogen and C$_{1-6}$alkyl;

R$_3$ is selected from hydrogen, hydroxy, C$_{1-6}$alkyl, C$_{2-6}$alkenyl, C$_{2-6}$alkynyl, C$_{1-6}$alkoxy, mercapto, halo, nitro and cyano;

n is 0, 1 or 2;

R$_4$ is selected from hydrogen, halo, hydroxy, cyano, nitro, C$_{1-6}$alkyl, halo-substituted-C$_{1-6}$alkyl, C$_{1-12}$alkoxy, halo-substituted-C$_{1-12}$alkoxy and —XR$_{10}$; wherein X is a bond or C$_{1-6}$alkylene, R$_{10}$ is selected from C$_{6-10}$aryl, C$_{5-10}$heteroaryl, C$_{3-12}$cycloalkyl and C$_{3-8}$heterocycloalkyl; wherein any aryl, heteroaryl, cycloalkyl or heterocycloalkyl of R$_{10}$ is optionally substituted with a radical selected from halo, hydroxy, cyano, nitro, C$_{1-6}$-alkyl, halo-substituted-C$_{1-6}$alkyl, C$_{1-6}$alkoxy and halo-substituted-C$_{1-6}$alkoxy;

m is 1, 2 or 3; and wherein the phenyl rings A and B can independently have up to four —C= groups replaced by —N=;

or the pharmaceutically acceptable salts thereof.

2. The compound of claim 1 in which:

W is N;

Y is C;

Z is a divalent radical selected from —C(O)NR$_5$— and —NR$_5$C(O)—; R$_5$ is selected from hydrogen and C$_{1-6}$alkyl;

R₁ is selected from hydrogen, halo, hydroxy and —NR₆R₇; wherein R₆ is selected from hydrogen and C₁₋₆alkyl; R₇ is selected from C₆₋₁₀aryl and C₅₋₁₀heteroaryl; or R₆ and R₇ together with the nitrogen to which both R₆ and R₇ are attached form C₃₋₈heterocycloalkyl; wherein any aryl, heteroaryl or heterocycloalkyl of R₇ or of the combination of R₆ and R₇ can be optionally substituted with 1 to 3 radicals selected from halo, cyano, C₁₋₆alkyl, C₂₋₆alkenyl, halo-substituted-C₁₋₆alkyl, halo-substituted-C₁₋₆alkoxy, —XNR₈R₈, —XC(O)NR₈R₈, —XC(O)NR₈XOR₈, —XS(O)₂NR₈R₈, —XSR₈, —XNR₈S(O)₂R₈, —XNR₈C(O)R₈, —XOC(O)R₈, —XOR₈ and —XOR₉; wherein X is a bond or C₁₋₆alkylene, R₈ is hydrogen or C₁₋₆alkyl, R₉ is C₆₋₁₀aryl;

R₂ is hydrogen or C₁₋₆alkyl;

R₃ is C₁₋₆alkyl;

n is 1; and

R₄ is selected from halo, halo-substituted-C₁₋₆alkyl, and —XR₁₀; wherein X is a bond or C₁₋₆alkylene, R₁₀ is selected from C₅₋₁₀heteroaryl and C₃₋₈heterocycloalkyl; wherein any heteroaryl or heterocycloalkyl of R₁₀ is optionally substituted with C₁₋₆alkyl; and m is 1, 2 or 3.

3. The compound of claim 2 in which Z is a divalent radical selected from —C(O)NH— and —NHC(O)—.

4. The compound of claim 2 in which R₁ is selected from hydrogen, halo, hydroxy and —NHR₇; wherein R₇ is selected from phenyl and pyridinyl; or R₆ and R₇ together with the nitrogen to which both R₆ and R₇ are attached form morpholino; wherein any aryl, heteroaryl or heterocycloalkyl of R₇ or of the combination of R₆ and R₇ can be optionally substituted with 1 to 3 radicals selected from halo, cyano, trifluoromethyl, trifluoromethoxy, dimethylamino, amino, aminocarbonyl, methyl-aminocarbonyl, aminosulfonyl, 1-hydroxy-ethyl, hydroxymethyl, acetoxy-methyl, methyl-sulfanyl, phenoxy, methyl-carboxy-methyl, butyl-amino-sulfonyl, methyl, isopropenyl, methoxy-ethyl-aminocarbonyl, 1-hydroxy-1-methyl-ethyl, methyl-sulfonyl-amino and methyl-carbonyl-amino; and R₃ is hydrogen or methyl.

5. The compound of claim 2 in which R₄ is selected from halo, trifluoromethyl and —XR₁₀; wherein X is a bond or methylene; R₁₀ is selected from imidazolyl, piperazinyl and morpholino; wherein any heteroaryl or heterocycloalkyl is optionally substituted with methyl.

6. The compound of claim 1 selected from: 4-(3-Trifluoromethyl-phenylamino)-pyrrolo[2,3-d]pyrimidine-7-carboxylic acid [3-(4-morpholin-4-yl-phenylcarbamoyl)-phenyl]-amide; 4-(4-Trifluoromethyl-1-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(3-Dimethylamino-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-(3-Carbamoyl-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(3-Sulfamoyl-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-[3-(1-Hydroxy-ethyl)-phenylamino]-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-(3-Carbamoyl-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-(3-Sulfamoyl-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-[3-(1-Hydroxy-ethyl)-phenylamino]-pyrrolo[2,3-d]pyrimidine-7-carboxylic acid [5-(3-fluoro-5-trifluoromethyl-benzoylamino)-2-methyl-phenyl]-amide; 4-Hydroxy-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-(4-Carbamoyl-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-(3-Hydroxymethyl-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; Acetic acid 3-(7-{2-methyl-5-[3-(4-methyl-imidazol-1-yl)-5-trifluoromethyl-benzoylamino]-phenylcarbamoyl}-7H-pyrrolo[2,3-d]pyrimidin-4-ylamino)-benzyl ester; Pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-(4-Trifluoromethyl-phenylamino)-pyrrolo[2,3-d]pyrimidine-7-carboxylic acid [3-(4-morpholin-4-yl-phenylcarbamoyl)-phenyl]-amide; 4-(4-Trifluoromethyl-phenylamino)-pyrrolo[2,3-d]pyrimidine-7-carboxylic acid [4-(4-morpholin-4-yl-phenylcarbamoyl)-phenyl]-amide; 4-(4-Trifluoromethoxy-phenylamino)-pyrrolo[2,3-d]pyrimidine-7-carboxylic acid [3-(4-morpholin-4-yl-phenylcarbamoyl)-phenyl]-amide; 4-(3-Bromo-phenylamino)-pyrrolo[2,3-d]pyrimidine-7-carboxylic acid [3-(4-morpholin-4-yl-phenylcarbamoyl)-phenyl]-amide; 4-(3-Dimethylamino-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(3-Bromo-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(3-Methylsulfanyl-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(Pyridin-3-ylamino)-pyrrolo[2,3-d]pyrimidine-7-carboxylic acid {2-methyl-5-[4-(4-methyl-piperazin-1-ylmethyl)-benzoylamino]-phenyl}-amide; 4-(3-Phenoxy-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(3-Hydroxymethyl-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(3-Butylsulfamoyl-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(4-Fluoro-2-methyl-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(3-Chloro-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-(3-Fluoro-phenylamino)-pyrrolo[2,3-d]pyrimidine-7-carboxylic acid {2-methyl-5-[4-(4-methyl-piperazin-1-ylmethyl)-benzoylamino]-phenyl}-amide; 4-m-Tolylamino-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-(3-Cyano-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-Chloro-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-Chloro-pyrrolo[2,3-d]pyrimidine-7-carboxylic acid {2-methyl-5-[4-(4-methyl-piperazin-1-ylmethyl)-benzoylamino]-phenyl}-amide; 4-(3-Isopropenyl-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-[3-(2-Methoxy-ethylcarbamoyl)-phenylamino]-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-[3-(1-Hydroxy-1-methyl-ethyl)-phenylamino]-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-[3-(1-Hydroxy-ethyl)-phenylamino]-pyrrolo[2,3-d]pyrimidine-7-carboxylic acid [5-(3-fluoro-5-trifluoromethyl-benzoylamino)-2-methyl-phenyl]-amide; 4-Chloro-pyrrolo[2,3-d]pyrimidine-7-carboxylic acid [2-methyl-5-(3-trifluoromethyl-benzoylamino)-phenyl]-amide; 4-Hydroxy-pyrrolo[2,3-d]pyrimidine-7-carboxylic acid [2-methyl-5-(3-trifluoromethyl-benzoylamino)-phenyl]-amide; 4-(3-Dimethylamino-phenylamino)-pyrrolo[2,3-d]pyrimidine-7-carboxylic acid [2-methyl-5-(3-trifluoromethyl-benzoylamino)-phenyl]-amide; 4-[3-(1-Hydroxy-ethyl)-phenylamino]-pyrrolo[2,3-d]pyrimidine-7-carboxylic acid [2-methyl-5-(3-trifluoromethyl-benzoylamino)-phenyl]-amide; 4-(3-Hydroxymethyl-phenylamino)-pyrrolo[2,3-d]pyrimidine-7-carboxylic acid [2-methyl-5-(3-trifluoromethyl-benzoylamino)-phenyl]-amide; 4-(3-Carbamoyl-phenylamino)-pyrrolo[2,3-d]pyrimidine-7-carboxylic acid [2-methyl-5-(3-trifluoromethyl-benzoylamino)-phenyl]-amide; 4-(3-Methanesulfonylamino-phenylamino)-pyrrolo[2,3-d]pyrimidine-7-carboxylic acid [2-methyl-5-(3-trifluoromethyl-benzoylamino)-phenyl]-amide; 4-(3-Acetylamino-phenylamino)-pyrrolo[2,3-d]pyrimidine-7-carboxylic acid [2-methyl-5-(3-trifluoromethyl-benzoylamino)-phenyl]-amide; 4-(3-Sulfamoyl-phenylamino)-pyrrolo[2,3-d]pyrimidine-7-carboxylic acid [2-methyl-5-(3-trifluoromethyl-benzoylamino)-phenyl]-amide; 4-(4-Carbamoyl-phenylamino)-pyrrolo[2,3-d]pyrimidine-7-carboxylic acid [2-methyl-5-(3-trifluoromethyl-benzoylamino)-phenyl]-amide; 4-(3-Methylcarbamoyl-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-(3-Acetylamino-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-(3-Methanesulfonylamino-phenylamino)-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-Morpholin-4-yl-pyrrolo[2,3-d]pyrimidine-7-carboxylic acid {2-methyl-5-[3-(4-methyl-imidazol-1-yl)-5-trifluoromethyl-benzoylamino]-phenyl}-amide; 4-Morpholin-4-yl-pyrrolo[2,3-d]pyrimidine-7-carboxylic acid [5-(3-fluoro-5-trifluoromethyl-benzoylamino)-2-methyl-phenyl]-amide; 4-(3-Dimethylamino-phenylamino)-pyrrolo[2,3-d]pyrimidine-7-carboxylic acid (3-{[3-(4-methyl-imidazol-1-yl)-5-trifluoromethyl-benzoylamino]-methyl}-phenyl)-amide; and 4-(3-Dimethylamino-phenylamino)-pyrrolo[2,3-d]pyrimidine-7-carboxylic acid {2-methyl-3-[3-(4-methyl-imidazol-1-yl)-5-trifluoromethyl-benzoylamino]-phenyl}-amide.

7. A pharmaceutical composition comprising a therapeutically effective amount of a compound of claim 1 in combination with a pharmaceutically acceptable excipient.

8. A method for treating lung carcinoma, comprising administering to a subject a therapeutically effective amount of a compound of claim 1.

* * * * *